US008481560B2

(12) United States Patent
Stinchcomb et al.

(10) Patent No.: US 8,481,560 B2
(45) Date of Patent: Jul. 9, 2013

(54) ABUSE DETERRENT TRANSDERMAL FORMULATIONS OF OPIATE AGONISTS AND AGONIST-ANTAGONISTS

(75) Inventors: Audra Lynn Stinchcomb, Lexington, KY (US); Guohua Li, Lexington, KY (US); Stan Lee Banks, Frankfort, KY (US); Jeffery Lynn Howard, Richmond, KY (US); Miroslaw Jerzy Golinski, Lexington, KY (US)

(73) Assignee: Alltranz Inc., Lexington, KY (US)

( * ) Notice: Subject to any disclaimer, the term of this patent is extended or adjusted under 35 U.S.C. 154(b) by 228 days.

(21) Appl. No.: 13/079,758

(22) Filed: Apr. 4, 2011

(65) Prior Publication Data
US 2011/0245783 A1 Oct. 6, 2011

Related U.S. Application Data

(60) Provisional application No. 61/320,526, filed on Apr. 2, 2010.

(51) Int. Cl.
*A61K 31/44* (2006.01)
*A61K 9/70* (2006.01)

(52) U.S. Cl.
USPC ............................ 514/282; 514/279; 424/449

(58) Field of Classification Search
USPC .................................. 514/282, 278; 424/449
See application file for complete search history.

(56) References Cited

U.S. PATENT DOCUMENTS

| 4,584,355 | A | 4/1986 | Blizzard et al. |
| 4,585,836 | A | 4/1986 | Homan et al. |
| 4,591,622 | A | 5/1986 | Blizzard et al. |
| 4,655,767 | A | 4/1987 | Woodard et al. |
| 7,867,986 | B2 | 1/2011 | Houze |
| 2002/0111377 | A1 | 8/2002 | Stinchcomb |
| 2005/0266061 | A1 | 12/2005 | Stinchcomb et al. |
| 2008/0008745 | A1 | 1/2008 | Stinchcomb et al. |
| 2008/0076789 | A1* | 3/2008 | Stinchcomb et al. .......... 514/282 |
| 2008/0233178 | A1* | 9/2008 | Reidenberg et al. .......... 424/449 |
| 2009/0017102 | A1 | 1/2009 | Stinchcomb et al. |
| 2009/0036523 | A1 | 2/2009 | Stinchcomb et al. |
| 2009/0082466 | A1* | 3/2009 | Babul ............................ 514/646 |
| 2009/0143462 | A1 | 6/2009 | Stinchcomb et al. |
| 2009/0246265 | A1* | 10/2009 | Stinchcomb et al. .......... 424/449 |
| 2010/0249045 | A1* | 9/2010 | Babul ........................... 514/21.4 |

OTHER PUBLICATIONS

U.S. Appl. No. 61/320,514, filed Apr. 2, 2010, Stinchcomb, et al.
U.S. Appl. No. 61/320,522, filed Apr. 2, 2010 Stinchcomb, et al.
Nalluri, et al., "In Vitro Release Studies on Matrix Type Transdermal Drug Delivery Systems of Naltrexone and Its Acetyl Prodrug", *Drug Development and Industrial Pharmacy*, vol. 31, 2005, pp. 871-877.
Satas, D., "15. Acrylic Adhesives", *Handbook of pressure sensitive adhesive technology*, ($2^{nd}$ ed.), Satas D., ed, 1989 New York, NY: Nostrand Reinhold. pp. 396-456.
Sobieski., L.A. et al., "18. Silicone Pressure Sensitive Adhesives", *Silicone Pressure Sensitive Adhesives, Handbook of pressure sensitive adhesive technology*. ($2^{nd}$ ed.), Satas. D., Ed. 1989, New York, NY: Van Reinhold, pp. 508-517.
Thong, et al., "Percutaneous Penetration Enhancers: An Overview", *Skin Pharmacology and Physiology*, 2007, vol. 20, No. 6, pp. 272-282.
United States Department of Health and Human Services, Substance Abuse and Mental Health Services Administration Office of Applied Studies, National Survey on Drug Use and Health, 2007. ICPSR23782-v3. Ann Arbor, MI: Inter-university Consortium for Political and Social Research [distributor], Jan. 4, 2013. doi: 10.3886/ICPSR23782.v3.

* cited by examiner

*Primary Examiner* — Raymond Henley, III
(74) *Attorney, Agent, or Firm* — Foley & Lardner LLP

(57) ABSTRACT

Described herein are abuse-resistant multi-layer transdermal patches comprising opioids and opioid prodrugs having a barrier layer located between the layer containing opioid or opioid prodrug and a layer containing an opioid antagonist or opioid antagonist prodrug.

30 Claims, 4 Drawing Sheets

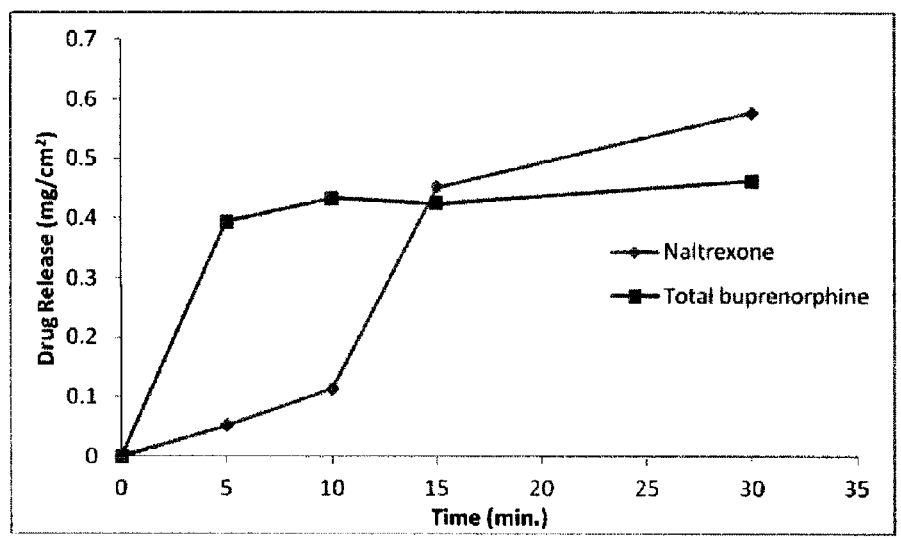
Figure 5. Release of NTX and total buprenorphine from buprenorphine prodrug:naltrexone patch (13% NTX-EC/HPC film, 5% BUP PD) in ethanol.
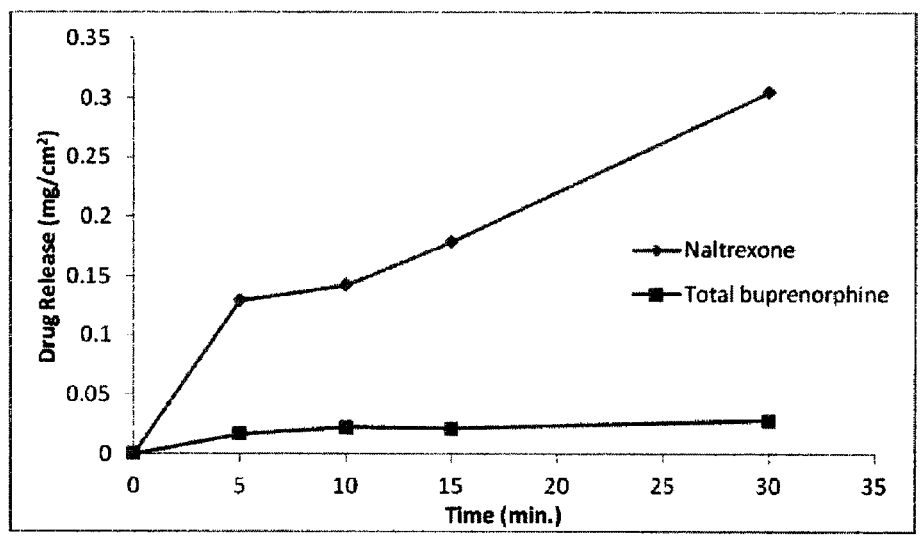
Figure 6. Release of NTX and total buprenorphine from buprenorphine prodrug:naltrexone patch (13% NTX-EC/HPC film, 5% BUP PD) in water.

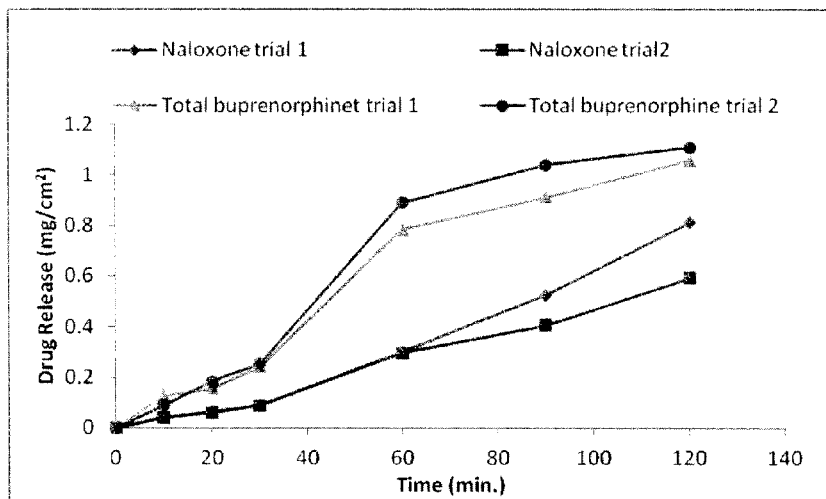
Figure 7. Release of NLX and total buprenorphine from buprenorphine prodrug:naloxone patch (10% NLX-EC/HPC film, 7% BUP PD) in ethanol.
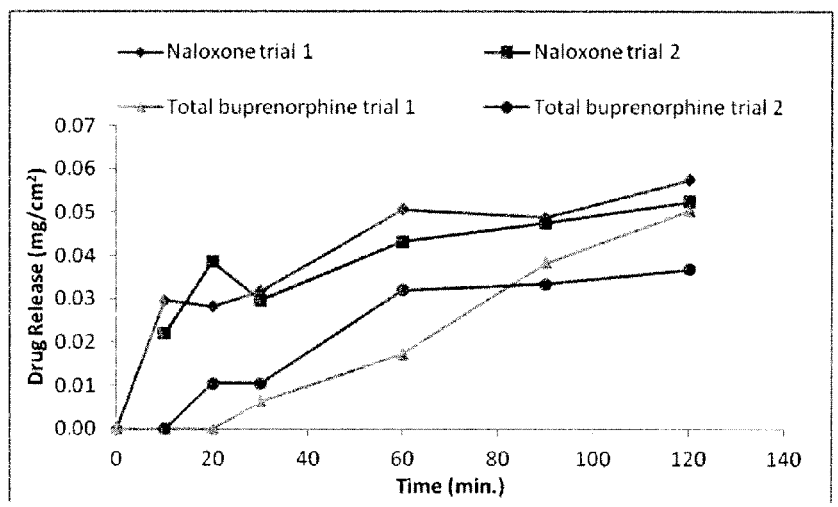
Figure 8. Release of NLX and total buprenorphine from buprenorphine prodrug:naloxone patch (10% NLX-EC/HPC film, 7% BUP PD) in water.

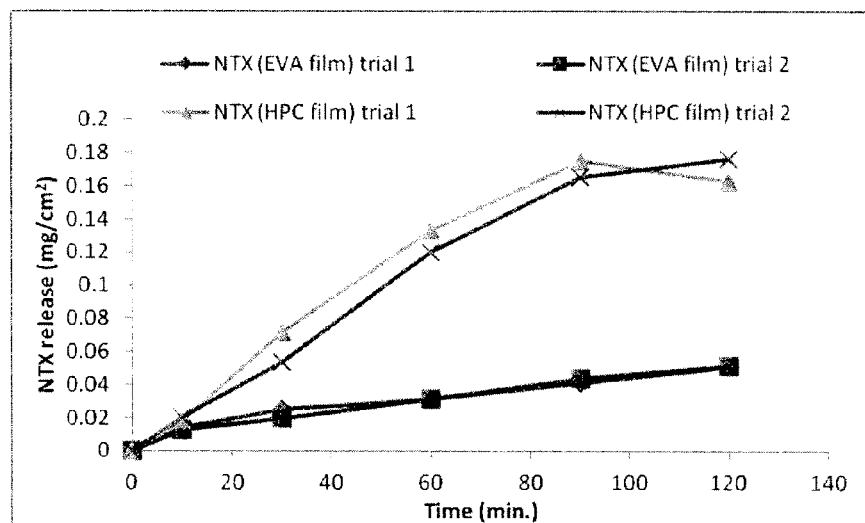
Figure 9. Release kinetics in ethanol from a 5% NTX ethylcellulose film using an ethylene vinyl acetate (EVA) membrane (3M™ Cotran™ 9728) or a prepared hydroxypropylcellulose membrane to separate the bi-layer system.

ABUSE DETERRENT TRANSDERMAL FORMULATIONS OF OPIATE AGONISTS AND AGONIST-ANTAGONISTS

CROSS REFERENCES TO RELATED APPLICATIONS

This application claims the benefit of U.S. Provisional Application Ser. No. 61/320,526, filed Apr. 2, 2010, which is incorporated herein by reference in its entirety.

FIELD

Described herein are opioid agonists, opioid agonist-antagonist or prodrugs of the foregoing in an abuse-resistant formulation and dosage form for transdermal delivery of the opioid agonist, opioid agonist-antagonist or prodrugs of the foregoing.

BACKGROUND

Pain is the most frequently reported symptom and is a common clinical problem confronting the clinician. Millions of people in the United States suffer from severe pain that, according to numerous recent reports, is chronically under-treated or inappropriately managed.

Opioids have long been recognized as one of the most effective treatments of pain. However, they also have a high potential of abuse. In fact, opioid and narcotic abuse are major worldwide problems connected with tremendous social and personal strife. As of 1992, the estimated United States economic cost of drug and alcohol abuse was $246 billion. A recent National Household Survey on Drug Abuse survey conducted by the Substance Abuse and Mental Health Services Administration reported in July 2007 that nearly one in twelve full-time workers in the United States have serious enough drug/alcohol problems to require medical treatment. Providing recovery assistance for drug addicts and alcoholics with pharmacological interventions has proven helpful.

Certain opioids, such as buprenorphine (BUP), butorphanol, dezocine, meptazinol, nalbuphine and pentazocine, have both agonist and antagonist qualities. For example, the main agonist-antagonist effect of buprenorphine is through its binding to μ-opioid and κ-opioid receptors, acting clinically as an agonist at lower doses and as an antagonist at higher doses. The dual agonist-antagonist activity of these opioids make them effective at not only treating pain, but also at reducing the severity of the withdrawal symptoms experienced when a former abuser begins to eliminate opioid and/or alcohol. Buprenorphine is currently available as a sublingual dosage form, both alone (Subutex®) and in combination with naloxone (Suboxone®) for the treatment of pain and opioid dependence. The sublingual administration of these formulations results in clinically relevant drawbacks. For example, the necessity of taking multiple daily doses, or even once-daily dosing, decreases patient compliance. In addition, the daily and multiple daily dosing necessary with sublingual dosage forms may cause more frequent and more extreme peaks and troughs in the blood-plasma concentration of the active medications. These peaks and troughs increase the potential for a patient to experience both the adverse effects associated with supra-therapeutic concentrations and ineffective relief associated with below therapeutic concentrations. Additionally, many sublingual tablets have a bitter taste, which reduces patient compliance.

Further, patients undergoing withdrawal from narcotic or alcohol abuse and those suffering from chronic, under-treated or intractable pain often also suffer from a lack of appetite, nausea and/or frequent emesis. As such, oral and sublingual therapies for these patients are often either poorly tolerated or fail to provide an effective therapeutic dose.

For these patients, transdermal administration can provide a favorable route of administration. Transdermal dosing provides the patient with a desirable systemic delivery profile which can minimize or eliminate any "highs" (dizziness and drowsiness) associated with more rapid absorption and can reduce the side effects associated with oral administration of a drug, such as abdominal pain, nausea and vomiting. Additionally, transdermal administration avoids first-pass metabolism which can allow for higher therapeutic concentrations to be achieved, and also offers a patient freedom from injections and surgical implantations. Transdermal delivery can also improve patient compliance by reducing the dose frequency. A transdermal patch can offer sustained release of a drug for an extended period (e.g., one week).

Because of the inherent potential for abuse, it is important that any pharmaceutical composition containing an opioid agonist or opioid agonist-antagonist or prodrugs of either be made as abuse-resistant or abuse-deterrent as possible. This is particularly true with extended release opioid products, including transdermal applications. Illicit users often will attempt to circumvent the extended release properties of these dosage forms by injecting, chewing or otherwise misusing or abusing the product in order to achieve an immediate release of the opioid agonist, opioid agonist-antagonist or prodrugs of the foregoing.

The Food and Drug Administration ("FDA") has recently emphasized the importance of reducing the risk of opioid abuse. In a Feb. 9, 2009 press release, the FDA publicly announced a program in which it would meet with the manufacturers of extended release and transdermal opioids regarding opioid misuse and abuse. Under the terms of the announced program, the manufactures will be required to develop Risk Evaluation and Mitigations Strategies to ensure proper opioid use.

Thus, it would be desirable to transdermally administer an opioid agonist or agonist-antagonist, such as buprenorphine, where the formulation or dosage form used to deliver the opioid agonist or agonist-antagonist is resistant to possible abuse or other illicit diversion.

SUMMARY

Some embodiments described herein, include an opioid agonist, agonist-antagonist or prodrugs of the foregoing, in an abuse resistant composition, formulation and dosage form (e.g., a patch) for transdermal delivery of the opioid.

Other embodiments, objects, features and advantages will be set forth in the detailed description of the embodiments that follows, and in part will be apparent from the description, or may be learned by practice, of the claimed invention. These objects and advantages will be realized and attained by the processes and compositions particularly pointed out in the written description and claims hereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

BRIEF DESCRIPTION OF THE DRAWINGS

FIG. 5 depicts the release profile of NTX and total buprenorphine from buprenorphine prodrug:naltrexone patch (13% NTX-EC/HPC film, 5% BUP PD) in ethanol.

FIG. 6 depicts the release profile of NTX and total buprenorphine from buprenorphine prodrug:naltrexone patch (13% NTX-EC/HPC film, 5% BUP PD) in water.

FIG. 7 depicts the release profile of NLX and total buprenorphine from buprenorphine prodrug:naloxone patch (10% NLX-EC/HPC film, 7% BUP PD) in ethanol.

FIG. 8 depicts the release profile of NLX and total buprenorphine from buprenorphine prodrug:naloxone patch (10% NLX-EC/HPC film, 7% BUP PD) in water.

FIG. 9 depicts the release kinetics in ethanol from a 5% NTX ethylcellulose film using an ethylene vinyl acetate (EVA) membrane (3M™ Cotran™ 9728) or a prepared hydroxypropylcellulose membrane to separate the bi-layer system.

DESCRIPTION

Figure 1:
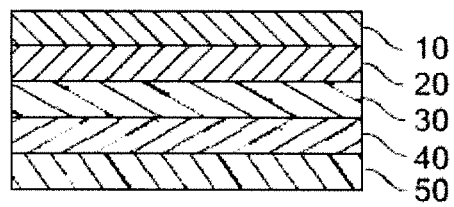
FIG. 1 is a cross-sectional view of a multi-layer transdermal delivery device.

While the present invention is capable of being embodied in various forms, the description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

As used herein the terms "abuse resistant" and "abuse deterrent" are synonymous and shall mean any pharmaceutical composition, formulation or dosage form that when misused, prevents the abuser from achieving the non-therapeutic effects sought from misuse of the composition, formulation or dosage form, such as opioid induced euphoria.

As used herein an "opioid" refers to compounds that affect opiate receptors, such as the mu, kappa, delta, epsilon, iota, lambda and zeta receptors and includes compounds and substances which activate opiate receptors ("opioid agonists"), inactivate or block opiate receptors ("opioid antagonist") and partially activate and partially inactivate or block opiate receptors ("opioid agonist-antagonists"). The term opioid also includes natural opiates, semi-synthetic opiates, fully synthetic opioids and endogenous opioid peptides, as well as prodrugs of such compounds. The term opioid also includes any pharmacologically acceptable salts of an opioid.

"Pharmaceutically acceptable salts," or "salts," include the salts of opioids suitable for administration to a mammal and includes those prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, tosylic, pamoic, napsylic, hydrobromic, valeric, oleic, lauric, salicylic, p-hydroxybenzoic, phenylacetic, mandelic, embonic, methanesulfonic, ethanesulfonic, benzenesulfonic, pantothenic, toluenesulfonic, 2-hydroxyethanesulfonic, sulfanilic, cyclohexylaminosulfonic, beta-hydroxybutyric, galactaric and galacturonic acids. The following list of pharmaceutically acceptable salts is not meant to be exhaustive but merely illustrative as person of ordinary skill in the art would appreciate that other pharmaceutically acceptable salts of opioids may be prepared.

In one embodiment, acid addition salts can be prepared from the free base forms through a reaction of the free base with a suitable acid. Suitable acids for preparing acid addition salts include both organic acids, e.g., acetic acid, propionic acid, glycolic acid, lactic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. The following list of organic and inorganic acids is not meant to be exhaustive but merely illustrative as person of ordinary skill in the art would appreciate that other acids may be used to create pharmaceutically acceptable salts of opioids. In other embodiments, an acid addition salt is reconverted to the free base by treatment with a suitable base. In still other embodiments, the basic salts are alkali metal salts, e.g., sodium salt.

As used herein, "prodrug" refers to a pharmacologically inactive (or significantly less active) chemical derivative that can be converted, enzymatically or non-enzymatically, in vivo or in vitro, to an active drug molecule, which is capable of exerting one or more physiological effects.

As used herein "substantially free of an opioid antagonist or prodrug of an opioid antagonist" shall mean that no opioid antagonist or prodrug of an opioid antagonist is separately added to the composition, or the respective element of the composition, when the composition is prepared and that any opioid antagonist or opioid antagonist prodrug which may be present is present in an amount which is sub-therapeutic. "Substantially free of an opioid antagonist or prodrug of an opioid antagonist" shall not mean that the no opioid antagonist or prodrug of an opioid antagonist is present in the composition or the respective element of the composition. For example, in one embodiment disclosed herein, a second layer of a patch formulation is substantially free of an opioid antagonist or prodrug of an opioid antagonist as these are not intentionally added to the second layer. However, the second layer may contain, through diffusion or other transport mechanism, an amount of an opioid antagonist or prodrug of an opioid antagonist due to its proximity with a first layer which may contain an opioid antagonist or a prodrug of an opioid antagonist.

As used herein a composition is "substantially free of water" when water has not been separately added to the composition, but may be present in the final composition as a result of the incorporation of other formulation components which contain water and the external absorption of the water from the environment. A composition is "substantially free of water" if water is present in an amount less than about 5% w/w, less than about 2% w/w, less than about 1% w/w, less than about 0.5% w/w or less than about 0.1% w/w of the composition.

As used herein "sub-therapeutic" shall mean an amount which is insufficient to elicit an observable pharmacologic response when administered to a subject.

Due to the potential for abuse by individuals addicted to opioids, it is desirable to incorporate such compounds into abuse-resistant or abuse-deterrent formulations and dosage forms so that the possibility of abuse through intravenous administration, inhalation, buccal absorption, oral ingestion or other methods of misuse of the dosage form (e.g., a transdermal patch) is substantially reduced or eliminated. For example, with transdermal administration, it is desirable to use poorly absorbed forms of opioid antagonists to minimize the effect of the opioid antagonist during transdermal use, but preserve the antagonist properties in the event that abuse of the dosage form is attempted.

In one embodiment shown in FIG. 1, the transdermal patch comprises a non-reactive backing layer 10, an opioid antagonist layer (or prodrug thereof) 20, a barrier layer 30, an opioid agonist/agonist-antagonist layer (or prodrug thereof) 40 and a removable film covering 50. The non-reactive backing layer 10 may be an occlusive backing, such as Cotran 9715 Film 3M™. Underlying the non-reactive backing layer 10 is the opioid antagonist (or prodrug thereof) layer 20. Next, the barrier layer 30 separates the opioid antagonist (or prodrug thereof) layer 20 from the opioid agonist/agonist-antagonist (or prodrugs thereof) layer 40. In one embodiment, the barrier layer 30 is a polymeric film or mixture of polymers that is substantially impermeable to opioid antagonists, opioid agonists and opioid agonist-antagonists thereby functioning to separate the contents of layer 20 from layer 40. The opioid agonist/agonist-antagonist (or prodrug thereof) layer 40 contains an opioid agonist, an opioid agonist-antagonist, an opioid agonist prodrug or an opioid agonist-antagonist prodrug. Underlying layer 40 is a removable film covering 50. Illustratively, Scotch Pack 1022 Release Liner 3.0 mil 3M™ may be used as a film covering. Prior to administration to a subject, the film covering 50 is removed and layer 40 is placed in direct contact with the subject's skin. In alternative embodiments layer 20 comprises one or more opioid antagonists while layer 40 comprises one or more opioid agonists or opioid agonist-antagonist or a combination of opioid agonists and agonist-antagonist. In another embodiments, layer 20 comprises one or more opioid antagonists while layer 40 comprises one or more opioid agonist prodrugs or opioid agonist-antagonist prodrugs or combination of opioid agonist prodrugs and agonist-antagonist prodrugs. In a further embodiment, layer 20 comprises one or more opioid antagonist prodrugs while layer 40 comprises one or more opioid agonists or opioid agonist-antagonist or combination of opioid agonist and agonist-antagonist. In an additional embodiment, layer 20 comprises one or more opioid antagonist prodrugs while layer 40 comprises one or more opioid agonist prodrugs or opioid agonist-antagonist prodrugs or combination of opioid agonist prodrugs and agonist-antagonist prodrugs.

Figure 2:
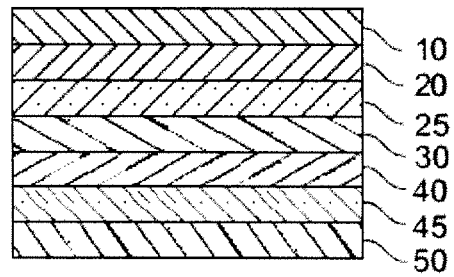
FIG. 2 is a cross-sectional view of a multi-layer transdermal delivery device.

FIG. 2 is another embodiment of a transdermal patch. The transdermal patch of FIG. 2 is similar to FIG. 1 apart from the addition to two adhesive layers 25 and 45. Adhesive layer 25 is in contact with and between the opioid antagonist layer 20 and the barrier layer 30; adhesive layer 45 is in contact with and located between layer 40 and the removable film covering 50. Illustrated in FIG. 2, the transdermal patch further comprises a non-reactive backing layer 10, an opioid antagonist layer 20, an adhesive layer 25, a barrier layer 30, an opioid agonist/agonist-antagonist layer 40, an adhesive layer 45 and a removable film covering 50.

Figure 3:
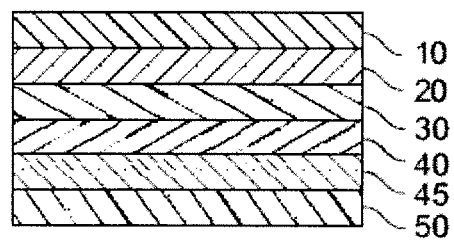
FIG. 3 is a cross-sectional view of a multi-layer transdermal delivery device.
Figure 4:
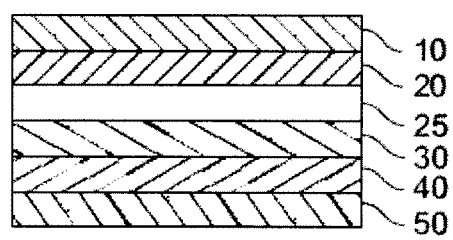
FIG. 4 is a cross-sectional view of a multi-layer transdermal delivery device.

A further embodiment shown in FIG. 3 is similar to the transdermal patch of FIG. 2 but contains only one additional adhesive layer 45. Likewise, FIG. 4 illustrates another embodiment that is similar to the transdermal patch of FIG. 2 but contains only one additional adhesive layer 25.

Upon visual examination of the transdermal patches of FIGS. 1-4, a potential opioid abuser would be unable to observe a physical distinction between the opioid antagonist layer 20, the barrier layer 30 and the opioid agonist/agonist-antagonist layer 40 after they are placed together. Thus, a potential abuser would not be able to differentiate layer 40 containing only the opioid agonist or the opioid agonist-antagonist from layer 20 containing the opioid antagonist, or their respective prodrugs.

In one embodiment, the opioid agonist/agonist-antagonist layer 40 has a thickness of between about 0.1 mil and about 100 mil; between about 1 mil and about 50 mil; between about 2 mil and about 20 mil; and between about 5 mil and about 20 mil. Illustratively, the opioid agonist/agonist-antagonist layer 40 may have a thickness of about 0.1 mil, about 0.2 mil, about 0.3 mil, about 0.4 mil, about 0.5 mil, about 0.6 mil, about 0.7 mil, about 0.8 mil, about 0.9 mil, 1 mil, about 2 mil, about 3 mil, about 4 mil, about 5 mil, about 6 mil, about 7 mil, about 8 mil, about 9 mil, about 10 mil, about 11 mil, about 12 mil, about 13 mil, about 14 mil, about 15 mil, about 16 mil, about 17 mil, about 18 mil, about 19 mil, about 20 mil, about 21 mil, about 22 mil, about 23 mil, about 24 mil, about 25 mil, about 26 mil, about 27 mil, about 28 mil, about 29 mil, about 30 mil, about 31 mil, about 32 mil, about 33 mil, about 34 mil, about 35 mil, about 36 mil, about 37 mil, about 38 mil, about 39 mil, about 40 mil, about 41 mil, about 42 mil, about 43 mil, about 44 mil, about 45 mil, about 46 mil, about 47 mil, about 48 mil, about 49 mil, about 50 mil, about 51 mil, about 52 mil, about 53 mil, about 54 mil, about 55 mil, about 56 mil, about 57 mil, about 58 mil, about 59 mil, about 60 mil, about 61 mil, about 62 mil, about 63 mil, about 64 mil, about 65 mil, about 66 mil, about 67 mil, about 68 mil, about 69 mil, about 70 mil, about 71 mil, about 72 mil, about 73 mil, about 74 mil, about 75 mil, about 76 mil, about 77 mil, about 78 mil, about 79 mil, about 80 mil, about 81 mil, about 82 mil, about 83 mil, about 84 mil, about 85 mil, about 86 mil, about 87 mil, about 88 mil, about 89 mil, about 90 mil, about 91 mil, about 92 mil, about 93 mil, about 94 mil, about 95 mil, about 96 mil, about 97 mil, about 98 mil, about 99 mil or about 100 mil.

The opioid agonist for use in layer 40 can be selected from the group comprising alfentanil, allylprodine, alphaprodine, anileridine, benzylmorphine, bezitramide, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, hydrocodone, hydromorphone, hydroxypethidine, isomethadone, ketobemidone, levorphanol, levomethadyl, levophenacylmorphan, lofentanil, meperidine, metazocine, methadone, metopon, morphine, myrophine, narceine, nicomorphine, norlevorphanol, normethadone, normorphine, norpipanone, opium, oxycodone, oxymorphone, papaveretum, phenadoxone, phenomorphan, phenazocine, phenoperidine, piminodine, piritramide, propheptazine, promedol, properidine, propoxyphene, sufentanil, tilidine, tramadol and salts of the foregoing. In another embodiment, the composition comprises pharmaceutically acceptable prodrugs of opioid agonist.

In another embodiment, an opioid agonist-antagonist for use in layer 40 can be selected from the group comprising buprenorphine, butorphanol, dezocine, meptazinol, nalbuphine, nalorphine, pentazocine and salts of the foregoing. In a further embodiment, the opioid agonist or agonist-antagonist is buprenorphine. In another embodiment, the composition comprises pharmaceutically acceptable prodrugs of opioid agonist or agonist-antagonists. In a further embodiment, the prodrug of the opioid agonist or agonist-antagonist is a prodrug of buprenorphine.

In another embodiment, illustrative opioid prodrugs of buprenorphine include those compounds of Formula (I):

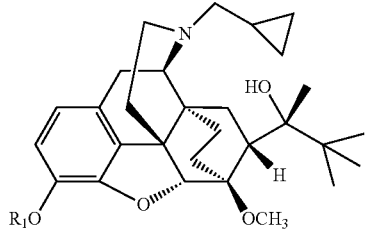

(I)

wherein $R_1$ is comprised of a bio-labile linker (e.g. ester, oxygenated ester, oxaester, pegylated ester, hydroxylated ester, non-hydroxylated ester, alkyl ester, amino ester, alkylamino ester, dialkylamino ester, carbonate, alkyl carbonate, oxygenated carbonate, pegylated carbonate, hydroxylated carbonate, non-hydroxylated carbonate, carbamate, alkyl carbamate, amino carbamate, alkylamino carbamate, dialkylamino carbamate or other suitable bio-labile linking structure) and further comprising moieties which can be selected in order to control the rate and extent of transdermal absorption and metabolism.

In additional embodiments of compounds of Formula (I), $R_1$ is an alkyl carbonate or an oxygenated alkyl carbonate. In a further embodiment $R_1$ is a hydroxylated alkyl carbonate. In another embodiment $R_1$ is an oxa-carbonate. In a further embodiment $R_1$ is a pegylated carbonate. In an additional embodiment $R_1$ is methyl carbonate. In further embodiments, $R_1$ can be an oxygenated alkyl carbonate and have 1 alkyl carbon, 2 alkyl carbons, 3 alkyl carbons, 4 alkyl carbons, 5 alkyl carbons, 6 alkyl carbons, 7 alkyl carbons, 8 alkyl carbons, 9 alkyl carbons, 10 alkyl carbons, 11 alkyl carbons, 12 alkyl carbons, 13 alkyl carbons, or 14 alkyl carbons. In a further embodiments, $R_1$ can be an alkyl carbonate and have 2 alkyl carbons, 3 alkyl carbons, 4 alkyl carbons, 5 alkyl carbons, 6 alkyl carbons, 7 alkyl carbons or 8 alkyl carbons. In further embodiments, $R_1$ can be a pegylated carbonate having 1 ethylene glycol repeat unit, 2 ethylene glycol repeat units, 3 ethylene glycol repeat units, 4 ethylene glycol repeat units, 5 ethylene glycol repeat units, 6 ethylene glycol repeat units, 7 ethylene glycol repeat units or 8 ethylene glycol repeat units. In further embodiments, the oxygenated alkyl carbonate has 1 oxygen atom, 2 oxygen atoms, 3 oxygen atoms, 4 oxygen atoms, 5 oxygen atoms, 6 oxygen atoms, 7 oxygen atoms, 8 oxygen atoms, 9 oxygen atoms, 10 oxygen atoms, 11 oxygen atoms or 12 oxygen atoms.

In a further embodiment $R_1$ is an oxygenated ester. In a further embodiment $R_1$ is an oxa-ester. In a further embodiment $R_1$ is a pegylated oxa-ester. In further embodiments, $R_1$ is a pegylated oxa-ester having 1 ethylene glycol repeat unit, 2 ethylene glycol repeat units, 3 ethylene glycol repeat units, 4 ethylene glycol repeat units, 5 ethylene glycol repeat units, 6 ethylene glycol repeat units, 7 ethylene glycol repeat units or 8 ethylene glycol repeat units. In a further embodiment, $R_1$ is an oxygenated alkyl ester. In a further embodiment $R_1$ is a hydroxylated alkyl ester. In further embodiments, $R_1$ is an oxygenated alkyl ester having 1 alkyl carbon, 2 alkyl carbons, 3 alkyl carbons, 4 alkyl carbons, 5 alkyl carbons, 6 alkyl carbons, 7 alkyl carbons, 8 alkyl carbons, 9 alkyl carbons, 10 alkyl carbons, 11 alkyl carbons, 12 alkyl carbons, 13 alkyl carbons, or 14 alkyl carbons. In further embodiments, the oxygenated esters have 1 oxygen atom, 2 oxygen atoms, 3 oxygen atoms, 4 oxygen atoms, 5 oxygen atoms, 6 oxygen atoms, 7 oxygen atoms, 8 oxygen atoms, 9 oxygen atoms, 10 oxygen atoms, 11 oxygen atoms or 12 oxygen atoms.

Several options for $R_1$ are disclosed herein. Also included herein are pharmaceutically acceptable forms of Formula (I), including the free base, salt, ester, hydrate, polymorph and derivatives of compounds of Formula I provided that the free base, salt, ester, hydrate, enantiomer, isomer, tautomer, polymorph or any other pharmacologically suitable derivative is, or becomes, a therapeutically active form of buprenorphine. The various options for $R_1$ also includes isomers of $R_1$, such as constitutional isomers, stereoisomers, enantiomers, diastereomers, and configurational diastereomers.

In a further embodiment, the buprenorphine prodrugs can be selected from the group comprising:

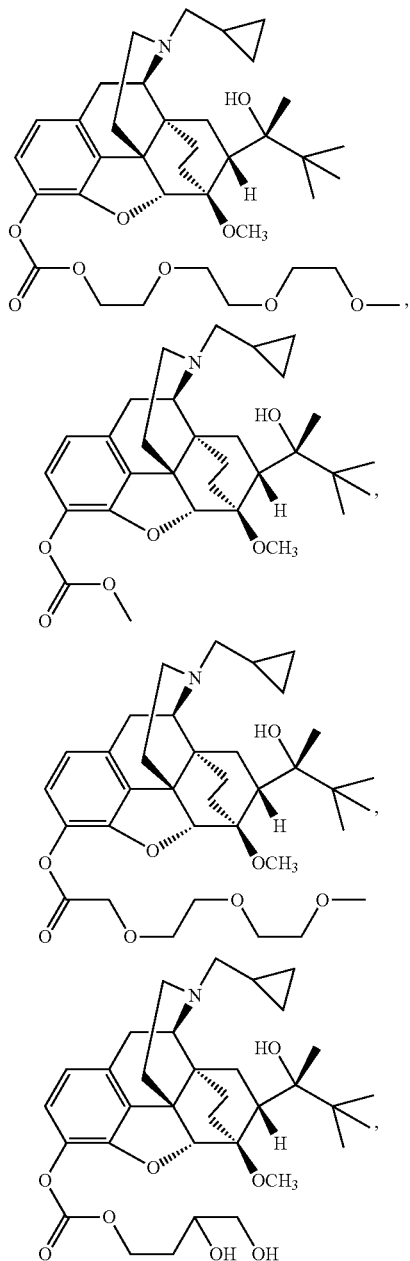

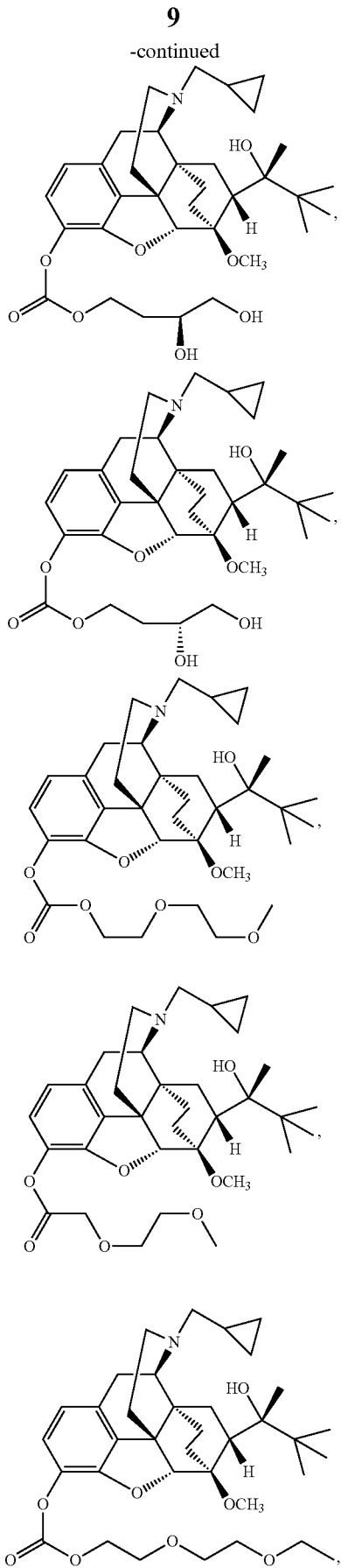

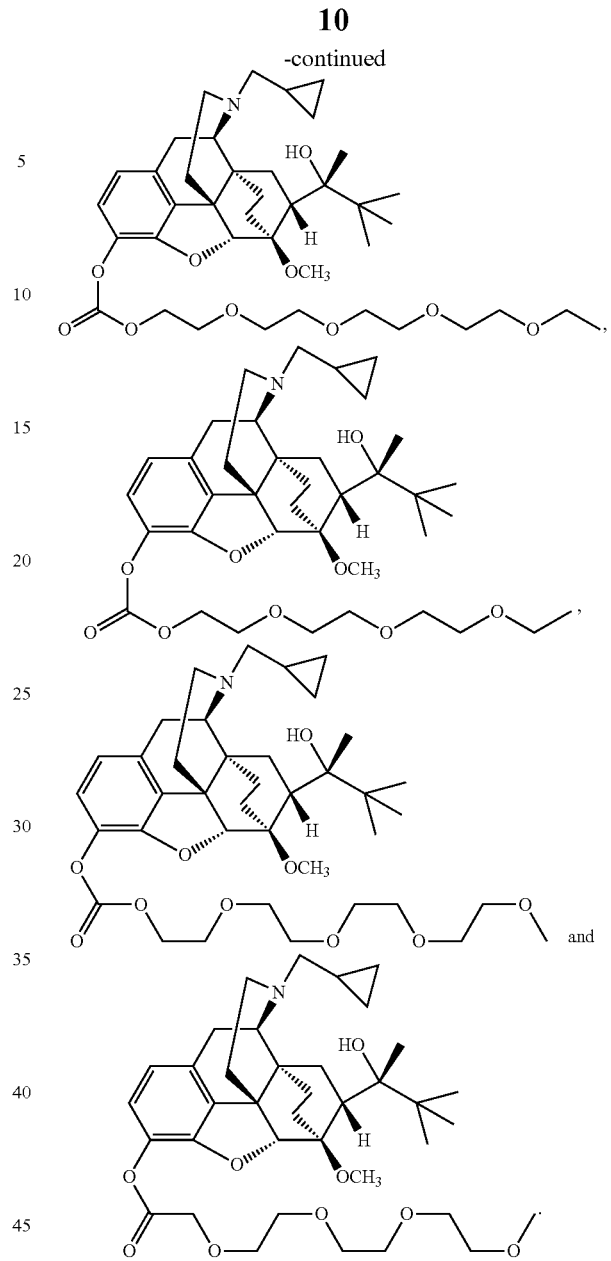

As described herein, buprenorphine prodrugs can be used with or instead of buprenorphine.

In another embodiment, the thickness of the opioid antagonist layer 20 may be increased to achieve longer wear time. In a further embodiment, the opioid antagonist layer 20 has a thickness of between about 0.1 mil and about 100 mil; between about 10 mil and about 75 mil; and between about 15 mil and about 60 mil. Illustratively, the opioid antagonist layer 20 may have a thickness of about 0.1 mil, about 0.2 mil, about 0.3 mil, about 0.4 mil, about 0.5 mil, about 0.6 mil, about 0.7 mil, about 0.8 mil, about 0.9 mil, 1 mil, about 2 mil, about 3 mil, about 4 mil, about 5 mil, about 6 mil, about 7 mil, about 8 mil, about 9 mil, about 10 mil, about 11 mil, about 12 mil, about 13 mil, about 14 mil, about 15 mil, about 16 mil, about 17 mil, about 18 mil, about 19 mil, about 20 mil, about 21 mil, about 22 mil, about 23 mil, about 24 mil, about 25 mil, about 26 mil, about 27 mil, about 28 mil, about 29 mil, about 30 mil, about 31 mil, about 32 mil, about 33 mil, about 34 mil, about 35 mil, about 36 mil, about 37 mil, about 38 mil, about 39 mil, about 40 mil, about 41 mil, about 42 mil, about 43 mil, about 44 mil, about 45 mil, about 46 mil, about 47 mil, about 48 mil, about 49 mil, about 50 mil, about 51 mil, about 52 mil, about 53 mil, about 54 mil, about 55 mil, about 56 mil, about 57 mil, about 58 mil, about 59 mil, about 60 mil, about 61 mil, about 62 mil, about 63 mil, about 64 mil, about 65 mil, about 66 mil, about 67 mil, about 68 mil, about 69 mil, about 70 mil, about 71 mil, about 72 mil, about 73 mil, about 74 mil, about 75 mil, about 76 mil, about 77 mil, about 78 mil, about 79 mil, about 80 mil, about 81 mil, about 82 mil, about 83 mil, about 84 mil, about 85 mil, about 86 mil, about 87 mil, about 88 mil, about 89 mil, about 90 mil, about 91 mil, about 92 mil, about 93 mil, about 94 mil, about 95 mil, about 96 mil, about 97 mil, about 98 mil, about 99 mil or about 100 mil.

In one embodiment, the opioid antagonist layer 20 comprises an opioid antagonist selected from the group consisting of: naltrexone ("NTX"), 6-beta-naltrexol, nalbuphine, nalmefene, naloxone ("NLX"), cyclazocine, levallorphan, cyclorphan, oxilorphan and prodrugs of the foregoing.

In a further embodiment, illustrative opioid antagonist prodrugs include those compounds of Formula (X):

Formula (X)

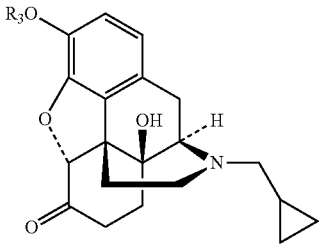

wherein $R_3$ is comprised of a bio-labile linker (e.g. ester, oxygenated ester, oxaester, pegylated ester, hydroxylated ester, alkyl ester, amino ester, alkylamino ester, dialkylamino ester, carbonate, alkyl carbonate, oxygenated carbonate, pegylated carbonate, hydroxylated carbonate, carbamate, alkyl carbamate, amino carbamate, alkylamino carbamate, dialkylamino carbamate or other suitable bio-labile linking structure) and further comprising moieties which can be selected in order to control the rate and extent of transdermal absorption and metabolism. Several options for $R_3$ are disclosed herein. Also included herein are pharmaceutically acceptable forms of Formula (X), including the free base, salt, ester, hydrate, polymorph and derivative of compounds of Formula I provided that the free base, salt, ester, hydrate, enantiomer, isomer, tautomer, polymorph or any other pharmacologically suitable derivative is, or becomes, a therapeutically active form of naltrexone. The various options for $R_3$ also includes isomers of $R_3$, such as constitutional isomers, stereoisomers, enantiomers, diastereomers, and configurational diastereomers.

In one embodiment, $R_3$ is selected from the group consisting of Formula (X), wherein $R_3$ is selected from the group consisting of:
—COC(CH$_3$)$_3$; —COCH(CH$_3$)$_2$; —COCH$_2$CH(CH$_3$)$_2$; —COCH(CH$_2$CH$_3$)$_2$; —CON(CH$_2$CH$_3$)$_2$; —CON(CH(CH$_3$)$_2$)$_2$; —COOCH(CH$_3$)$_2$;

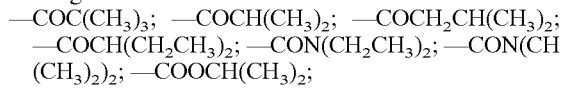

and —CO(CH$_2$)$_2$OCH$_3$.

As described herein, prodrugs of naltrexone and/or naloxone can be used with or instead of naltrexone and/or naloxone, respectively.

In a further embodiment, the opioid antagonist/antagonist prodrug layer 20 can further comprise a water-insoluble polymeric material and/or a water-soluble polymer used in preparing the barrier layer 30 and described in further detail below. The water-insoluble polymeric material and/or a water-soluble polymer added to layer 20 can be materials suitable for use in the barrier layer 30, even though the materials are not actually present in a particular embodiment of the barrier layer 30. In one embodiment, the combined total weight percent of the water-insoluble polymeric material and a water-soluble polymer to be included in layer 20 is between about 1-99%, about 5-95%, about 5-40%, about 5-20%, about 10-90%, about 10-30%, about 15-85%, about 15-25%, about 20-80%, about 25-45%, about 30-70%, 35-80%, 40-90%, 50-80% or about 60-95% of layer 20. In a further embodiment, the combined total weight percent of the water-insoluble polymeric material and a water-soluble polymer to be included in layer 20 is between about 1%, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 99% of layer 20.

The barrier layer 30 shown in FIGS. 1-4 is generally located between layer 20 and layer 40, although the barrier layer 30 may not be in contact with either layer 20 or 40, the barrier layer 30 may be in contact with only one of layers 20 or 40 or the barrier layer may be in contact with both layers 20 and 40.

The barrier layer 30 is located between layer 20 and layer 40 in FIG. 1, between layer 25 and layer 40 in FIG. 2, between layer 20 and layer 40 in FIG. 3 and between layer 25 and layer 40 in FIG. 4. The barrier layer 30 functions to separate the layers on either side of the barrier from contacting one another and to prevent the diffusion of opioid antagonist or opioid antagonist prodrug from layer 20 into layer 40.

In one embodiment the barrier layer 30 is comprised of a polymeric film. In a further embodiment, the polymeric film is comprised of a mixture of a water-insoluble polymeric material and a water-soluble polymer. In a further embodiment, the water soluble polymer is suitable for forming pores or other openings in the water-insoluble polymeric material to allow the opioid antagonist (or prodrug thereof) a possible route of egress from layer 20 of the transdermal patch upon misuse or abuse.

The water-insoluble polymeric material can be selected from the group consisting of: cellulose derivatives, such as ethyl cellulose (EC), cellulose esters, ethylene-vinyl acetate copolymer (EVA), polyolefins such as polyethylene, low density polyethylene (LDPE), medium density polyethylene (MDPE), high density polyethylene (HDPE), polypropylene, ethylene-propylene copolymers, styrene polymers such as polystyrene, vinyl polymers, polyvinyl acetate, and the like, acrylic polymers, such as ethylenemethyl acrylate copolymer, polymethyl acrylate, polyethyl acrylate, ethylene-acrylic acid copolymer, ethylene-ethylacrylate copolymer, homopolymers and copolymers of acrylic acid, methyl methacrylate and combinations thereof, and methyl acrylic acid esters with quaternary ammonium groups, such as Eudragit NE, RS, RL and the like. The water-insoluble polymeric material can also be combinations of the foregoing.

The water-insoluble polymeric material comprises between about 1-99%, about 5-95%, about 10-90%, about 15-85%, about 20-80%, about 30-70%, 35-80%, 40-90%, 50-80% or about 60-95% of the barrier layer. In additional embodiments, the water-insoluble polymeric material comprises between about 1%, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 99% of the barrier layer.

Water-soluble polymers suitable for use with the water-insoluble polymeric material for barrier layer 30 are selected from the group consisting of: cellulose derivatives such as hydroxypropylcellulose (HPC), hydroxypropylmethylcellulose (HPMC), hydroxyethylcellulose (HEC), methyl cellulose (MC), cellulose gum, sodium carboxymethylhydroxyethylcellulose, methylhydroxyethylcellulose (MHEC), carboxyalkylcelluloses such as carboxymethylcellulose (CMC), Benecel®, Culminal® polyvinylpyrrolidone (PVP), polyethylene oxide (PEO), polysaccharides such as dextran or polysialic acid (PSA), natural water-soluble polymers such as, corn starch, natural gums such as agar, agarose, alginates, xanthan gums, heparin, chitin, and chitosan, cellulose derivatives, polyvinyl alcohol, polyethylene glycol, polyoxazoline, poly acryloylmorpholine, and the like.

The water-soluble polymer(s) in the barrier layer comprises between about 1-99%, about 5-95%, about 5-40%, about 10-90%, about 10-30%, about 15-85%, about 20-80%, about 25-45%, about 30-70%, 35-80%, 40-90%, 50-80% or about 60-95% of the barrier layer. In further embodiments, the pore-forming water-soluble polymer(s) in the barrier layer comprises between about 1%, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 99% of the barrier layer.

In one embodiment, the barrier layer 30 comprises about 20% hydroxypropylcellulose and about 80% ethylcellulose by weight on dry basis. In another embodiment, the barrier layer 30 comprises about 10% hydroxypropylcellulose and about 90% ethylcellulose by weight on dry basis. In other embodiments, the barrier layer 30 comprises about 5-35% hydroxypropylcellulose and about 65-95% ethylcellulose by weight on dry basis. In other embodiments, the barrier layer 30 comprises about 10-30% hydroxypropylcellulose and about 70-90% ethylcellulose by weight on dry basis.

Ethylcellulose (EC) is a water-insoluble ether and available in four ethoxyl types from Hercules Inc. (K-, N-, T- and X-type). This polymer, containing about 46-48% or more of ethoxyl groups, is freely soluble in ethanol. Hydroxypropylcellulose (HPC) is a water-soluble pore former and usually incorporated into the rate-controlling EC membrane to modulate drug release from EC films. HPC is soluble in both aqueous and polar organic solvents. Klucel Pharm HPC is available in E, L, J, G, M and H viscosity types.

After soaking films in water or ethanol, numerous pores can be formed because low molecular weight HPC is an effective pore former. Films comprising EC and HPC were shown to be suitable as drug release modulator over naltrexone and/or naloxone, or salt forms of the foregoing.

This barrier layer 30 functions to separate layer 20 from layer 40. In one embodiment the barrier layer 30 is substantially impermeable to the contents of the layers 20 and 40. The selection of the barrier layer materials is such that the barrier layer is capable of preventing release of the opioid antagonist from the transdermal patch system while a patient is using the patch for transdermal opioid therapy. However, the selection of barrier layer materials should provide a sufficiently rapid rate of release of the opioid antagonist from the patch in order to block the euphoric effect or "high" obtained by an individual attempting to abuse or misuse the transdermal patch.

In a further embodiment, the barrier layer 30 further includes a plasticizer. A suitable plasticizer can be selected from the group consisting of: polyethylene glycol, propylene glycol, di-n-butylphthalate, glycerol, triethyl citrate, dibutyl phthalate, diethyl phthalate, paraffinic process oils, naphthenic process oils, aromatic process oils, and the like, squalane, squalene, olive oil, camellia oil, castor oil, tall oil, peanut oil, silicone oils, mineral oil, oleyl alcohol and the like, dioctyl phthalate, and the like, polybutene, liquid isoprene rubber, isopropyl myristate, hexyl laurate, diethyl sebacate, diisopropyl sebacate, diethylene glycol, glycol salicylate, dipropylene glycol, triacetin, crotamiton and the like, glycerol, oleic acid, and the like.

The non-reactive backing layer 10 is substantially impermeable to the opioid antagonist (or opioid antagonist prodrug) and other components of the multi-layer patch. Because the backing layer 10 is substantially impermeable to the opioid antagonist (or opioid antagonist prodrug), it prevents diffusion or other transport of the opioid antagonist (or antagonist prodrug) through the backing layer 10 even when the transdermal patch described herein has been placed in a solvent (e.g., water or ethanol) for attempted abuse or misuse of the transdermal patch. As used in association with the backing layer 10, the phrase "substantially impermeable" means that the contents of the transdermal patch (e.g., an opioid antagonist or opioid antagonist prodrug) are less likely to permeate, diffuse or otherwise transported through the backing layer 10 and be separated from the transdermal patch. Further, even though the backing layer 10 is substantially impermeable to the contents of the transdermal patch, some contents of the patch may pass through the backing layer 10; however, it is intended that the amount of material diffusing through the backing layer 10 be negligible relative to the overall contents and function of the patch. Moreover, because the backing layer 10 is substantially impermeable, any unintended diffusion through the backing layer 10 would not be a significant route of material (e.g., the opioid antagonist or antagonist prodrug) leaving the patch under conditions of anticipated use (transdermal delivery of an opioid) or misuse/abuse (e.g., placing in a solvent such as water or alcohol to extract the opioid agonist) of the patch.

The backing layer 10 may be made of a single layer or film of polymer, or be a laminate of one or more polymer layers. Preferably, the backing layer 10 has high flexibility, good oxygen transmission and high moisture-vapor transmission rate. Non-limiting examples of polymers suitable for use in the backing layer 10 are polyurethane, polyvinylchloride, polyvinylidene chloride, polyolefins such as ethylene-vinyl acetate copolymers, polyethylene, and polypropylene, and polyesters such as polyethyleneterephthalate. Additional examples of the backing layer 10 include CoTran 9701 Film 3M™, CoTran 9702 Film 3M™, CoTran 9706 Film 3M™, CoTran 9715 Film 3M™, CoTran 9720 Film 3M™, CoTran 9722 Film 3M™, Foam Tape 9772L 3M™, Foam Tape 9773 3M™, Scotchpak™ 1006, Scotchpak™ 1109, Scotchpak™ 9723, Scotchpak™ 9732 and Scotchpak™ 9733.

The adhesive layers 25 and 45 are formed from standard pressure sensitive adhesives known in the art. Non-limiting examples of pressure sensitive adhesives include polymer and copolymers of polyacrylates, polysiloxanes, polyisobutylene, polyisoprene, polybutadiene, ethylene-vinyl acetate and styrenic block polymers, such as styrene-isoprene-styrene block copolymer, styrene-butadiene-styrene copolymer, styrene-ethylenebutene-styrene copolymers, styrene-ethylene/propylene-styrene copolymers and di-block analogs thereof. Examples of polyacrylates include, but are not limited to, acrylic acids, alkyl acrylates and methacrylates; for example, acrylic acid, methacrylic acid, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate, methoxyethyl methacrylate, vinylacetate/ethylene acrylate and the like. Additional examples of appropriate acrylic adhesives suitable in the practice of the invention are described in Satas, "Acrylic Adhesives," Handbook of Pressure-Sensitive Adhesive Technology, 2nd ed., pp. 396-456 (D. Satas, ed.), Van Nostrand Reinhold, New York (1989).

Other useful pressure sensitive adhesives (PSA) can include mixtures of different polymers or mixtures of polymers such as synthetic rubber polyisobutylene (PIB), The PIB adhesives normally include a tackifier such as polybutene oil and resins such as the ESCOREZ® resins available from Exxon Chemical. Other useful rubber-based pressure-sensitive adhesives include hydrocarbon polymers such as natural and synthetic polyisoprene, polybutylene and polyisobutylene, styrene/butadiene polymers styrene-isoprene-styrene block copolymers, hydrocarbon polymers such as butyl rubber, halogen-containing polymers such as polyacrylic-nitrile, polytetrafluoroethylene, polyvinylchloride, polyvinylidene chloride, and polychlorodiene, and other copolymers thereof. Additional suitable pressure sensitive adhesives can be found in U.S. Pat. No. 7,867,986 which is hereby incorporated by reference in its entirety. Polyisobutylene polymers are available commercially under the trademark name VISTANEX® from Exxon Chemical.

Silicone-based pressure sensitive adhesives are also suitable for use in additional embodiments described herein. Suitable silicone-based pressure-sensitive adhesives can include those described in Sobieski, et al., "Silicone Pressure Sensitive Adhesives," Handbook of Pressure-Sensitive Adhesive Technology, 2nd ed., pp. 508-517 (D. Satas, ed.), Van Nostrand Reinhold, New York (1989), incorporated by reference in its entirety. Other useful silicone-based pressure sensitive adhesives are described in the following U.S. Pat. Nos. 4,591,622; 4,584,355; 4,585,836; and 4,655,767 which are hereby incorporated by reference in their entirety. Suitable silicone-based pressure-sensitive adhesives are commercially available and include the silicone adhesives sold under the trademarks BIO-PSA 7-4503, BIO-PSA 7-4603, BIO-PSA 7-4301, 7-4202, 7-4102, 7-4106, and BIO-PSA 7-4303 by Dow Corning Corporation, Medical Products, Midland, Mich. The commercially available silicones are sold under the trademark of BIO-PSA such as Bio-PSA 7-4102, 7-4202, 7-4302, 7-4101, 7-4201, 7-4301, 7-4303, 7-4503, 7-4603 by Dow Corning Cooperation. In one embodiment, amine-compatible Bio-PSA silicone adhesives are preferred. In a further embodiment, the preferred amine-compatible Bio-PSA silicone adhesive 7-4202 was employed in combination with acrylic adhesive such as Duro-tak 87-9301 manufactured by National Starch and Chemical Company.

In one embodiment a pressure sensitive adhesive is optionally used to assist in affixing a patch containing an opioid to be transdermally delivered to the subject. In a further embodiment, the pressure sensitive adhesive is present in a total amount by weight between about 1% and about 99.9%; between about 50% and about 99.9% and between about 75% and about 99.9%. In a further embodiment the pressure sensitive adhesive layer is a mixture of two or more pressure sensitive adhesives. In another embodiment, the pressure sensitive adhesive is a mixture of Bio-PSA silicone adhesive 7-4201 and Duro-Tak 87-9301 (manufactured by Dow Corning Corporation, Medical Products, Midland, Mich. and the National Starch and Chemical Company, respectively) which are mixed in a ratio of about 10:1 (7-4202:87-9301).

The removable film covering 50 is a protective layer made of a polymeric material that may be optionally metalized. Examples of polymeric materials include, but not limited to, polypropylene, polystyrene, polyurethane, polyethylene, polyimide, polyethylene terephthalate, polybutylene terephthalate, polyvinyl chloride, ethyl vinyl acetate, paper and the like. Illustratively, Scotch Pack 1022 Release Liner 3.0 mil 3M™ and Scotch Pack 9742 Release Liner 3M™

Additional embodiments include pharmaceutical compositions, formulations and dosage forms containing an opioid such as buprenorphine or a prodrug of buprenorphine, respectively, and an opioid antagonist or an opioid antagonist prodrug. In a further embodiment, the opioid antagonist is selected from the group consisting of: naltrexone ("NTX"), 6-beta-naltrexol, nalbuphine, nalmefene, naloxone ("NLX"), cyclazocine, levallorphan, cyclorphan, oxilorphan and prodrugs of the foregoing.

In one embodiment, the opioid antagonist would not be absorbable at a therapeutic rate or extent through the stratum corneum. In a further embodiment, when the pharmaceutical composition, formulation or dosage form is used properly, the rate at which the opioid antagonist is absorbed across the skin is insufficient to attenuate the unintended or adverse effects of opioid agonist or agonist-antagonist administration, such as anti-analgesia, hyperalgesia, hyperexcitability, physical dependence, physical tolerance, somnolence and constipation. In a further embodiment, when the pharmaceutical composition, formulation or dosage form is used properly, the rate at which the opioid antagonist is absorbed across the skin is insufficient to enhance the intended pharmacologic effects of the opioid agonist or agonist-antagonist, including the analgesic potency of the opioid agonist or agonist-antagonist.

In a further embodiment, the amount of the opioid antagonist in the pharmaceutical composition, formulation or dosage form is sufficient to block the pharmacological effect of the opioid agonist or agonist-antagonist if the composition, formulation or dosage form is misused or abused. In another embodiment, the amount of opioid antagonist in the pharmaceutical composition, formulation or dosage form is insufficient to limit the pharmacological activity of the opioid agonist or agonist-antagonist when the dosage form is used properly. In an additional embodiment, the ratio of opioid agonist or agonist-antagonist to opioid antagonist in the pharmaceutical composition, formulation or dosage form is sufficient to block the pharmacological activity of the opioid agonist or agonist-antagonist if the composition, formulation or dosage form is misused or abused, but will not block the pharmacological activity of the opioid agonist or agonist-antagonist when the dosage form is used properly.

In one embodiment, the ratio of opioid agonist or agonist-antagonist (or prodrugs thereof) to opioid antagonist (or prodrug thereof) in the pharmaceutical composition, formulation or dosage form is about 1 to about 60; 1 to about 50; 1 to about 40; 1 to about 30; 1 to about 20; about 1 to about 10; about 2 to about 10; about 3 to about 10; about 4 to about 10; about 5 to about 10; about 6 to about 10; about 7 to about 10; about 8 to about 10; about 9 to about 10; about 1 to about 9; about 2 to about 9; about 3 to about 9; about 4 to about 9; about 5 to about 9; about 6 to about 9; about 7 to about 9; about 8 to about 9; about 1 to about 8; about 2 to about 8; about 3 to about 8; about 4 to about 8; about 5 to about 8; about 6 to about 8; about 7 to about 8; about 1 to about 7; about 2 to about 7; about 3 to about 7; about 4 to about 7; about 5 to about 7; about 6 to about 7; about 1 to about 6; about 2 to about 6; about 3 to about 6; about 4 to about 6; about 5 to about 6; about 1 to about 5; about 2 to about 5; about 3 to about 5; about 4 to about 5; about 1 to about 4; about 2 to about 4; about 3 to about 4; about 1 to about 3; about 2 to about 3; about 1 to about 2 or about 1 to about 1.

In a further embodiment, the ratio of opioid antagonist to opioid agonist or agonist-antagonist in the pharmaceutical composition, formulation or dosage form is between about 1 to about 60 and about 1 to about 1; about 1 to about 40 and about 1 to about 20; and about 1 to about 15 and about 1 to about 10.

In a further embodiment, the ratio of opioid antagonist to opioid agonist or agonist-antagonist in the pharmaceutical composition, formulation or dosage form is about 1 to about 60; 1 to about 50; 1 to about 40; 1 to about 30; 1 to about 20; about 1 to about 10; about 2 to about 10; about 3 to about 10; about 4 to about 10; about 5 to about 10; about 6 to about 10; about 7 to about 10; about 8 to about 10; about 9 to about 10; about 1 to about 9; about 2 to about 9; about 3 to about 9; about 4 to about 9; about 5 to about 9; about 6 to about 9; about 7 to about 9; about 8 to about 9; about 1 to about 8; about 2 to about 8; about 3 to about 8; about 4 to about 8; about 5 to about 8; about 6 to about 8; about 7 to about 8; about 1 to about 7; about 2 to about 7; about 3 to about 7; about 4 to about 7; about 5 to about 7; about 6 to about 7; 1 to about 6; about 2 to about 6; about 3 to about 6; about 4 to about 6; about 5 to about 6; about 1 to about 5; about 2 to about 5; about 3 to about 5; about 4 to about 5; about 1 to about 4; about 2 to about 4; about 3 to about 4; about 1 to about 3; about 2 to about 3; about 1 to about 2 or about 1 to about 1.

The transdermal patch compositions described herein can be subject to abuse, misuse or otherwise diverted from proper use by opioid-dependent individuals. Frequently employed methods of abuse or misuse may involve chewing the transdermal patch or attempting to dissolve the opioid agonist in a suitable solvent (e.g., water, ethanol, turpentine, acetone, nail polish remover) so that the solubilized opioid can then be swallowed, injected or otherwise ingested by the opioid-dependent individual. In view of this, one embodiment described herein is a patch which, when placed in a solvent, releases both the agonist and antagonist from the patch and into the solvent at rates such that the ratio between the agonist and antagonist creates an opioid blockade and effectively prevents the opioid-dependent individual from obtaining opioid induced euphoria or other opioid "high" through misuse or abuse of the opioid-containing transdermal patch. The mass ratio of opioid agonist (or prodrug thereof) or agonist-antagonist (or prodrug thereof) to opioid antagonist (or prodrug thereof) in a solvent after a defined period of time is the release ratio.

When placed in water, the transdermal patch compositions described herein will release about 0%, about 1%, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100% of the opioid agonist (or prodrug thereof) or agonist-antagonist (or prodrug thereof) from the patch and into the water after about 30 seconds, about 1 minute, about 2 minutes, about 3 minutes, about 4 minutes, about 5 minutes, about 10 minutes, about 15 minutes, about 20 minutes, about 30 minutes, about 60 minutes, about 90 minutes or about 120 minutes.

When placed in water, the transdermal patch compositions described herein will release about 0%, about 1%, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100% of the opioid antagonist (or prodrug thereof) from the patch and into the water after about 30 seconds, about 1 minute, about 2 minutes, about 3 minutes, about 4 minutes, about minutes, about 10 minutes, about 15 minutes, about 20 minutes, about 30 minutes, about 60 minutes, about 90 minutes or about 120 minutes.

When a transdermal patch composition described herein is placed in water, the mass to mass ratio (release ratio) of (a) opioid agonist (or prodrug thereof) or opioid agonist-antagonist (or prodrug thereof) in the water to (b) opioid antagonist (or prodrug thereof) in the water will be about 1:60 to about 60:1, such as about 1:60; 1:55; 1:50; 1:45; 1:40; 1:35; 1:30; 1:25; 1:20; 1:15; 1:10; 1:5; 1:4; 1:3; 1:2; 1:1; 2:1; 3:1; 4:1; 5:1; 10:1; 15:1; 20:1; 25:1; 30:1; 35:1; 40:1; 45:1; 50:1; 55:1 and 60:1 after about 30 seconds, about 1 minute, about 2 minutes, about 3 minutes, about 4 minutes, about 5 minutes, about 10 minutes, about 15 minutes, about 20 minutes, about 30 minutes, about 60 minutes, about 90 minutes or about 120 minutes.

When placed in a 0.1 M phosphate buffer (pH 6.5), the transdermal patch compositions described herein will release about 0%, about 1%, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100% of the opioid agonist (or prodrug thereof) or agonist-antagonist (or prodrug thereof) from the patch and into the buffer after about 30 seconds, about 1 minute, about 2 minutes, about 3 minutes, about 4 minutes, about 5 minutes, about 10 minutes, about 15 minutes, about 20 minutes, about 30 minutes, about 60 minutes, about 90 minutes or about 120 minutes.

When placed in a 0.1 M phosphate buffer (pH 6.5), the transdermal patch compositions described herein will release about 0%, about 1%, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100% of the opioid antagonist (or prodrug thereof) from the patch and into the buffer after about 30 seconds, about 1 minute, about 2 minutes, about 3 minutes, about 4 minutes, about 5 minutes, about 10 minutes, about 15 minutes, about 20 minutes, about 30 minutes, about 60 minutes, about 90 minutes or about 120 minutes.

When a transdermal patch composition described herein is placed in a 0.1 M phosphate buffer (pH 6.5), the mass to mass ratio (release ratio) of (a) opioid agonist (or prodrug thereof) or opioid agonist-antagonist (or prodrug thereof) in the buffer to (b) opioid antagonist (or prodrug thereof) in the buffer will be about 1:60 to about 60:1, such as about 1:60; 1:55; 1:50; 1:45; 1:40; 1:35; 1:30; 1:25; 1:20; 1:15; 1:10; 1:5; 1:4; 1:3; 1:2; 1:1; 2:1; 3:1; 4:1; 5:1; 10:1; 15:1; 20:1; 25:1; 30:1; 35:1; 40:1; 45:1; 50:1; 55:1 and 60:1 after about 30 seconds, about 1 minute, about 2 minutes, about 3 minutes, about 4 minutes, about 5 minutes, about 10 minutes, about 15 minutes, about 20 minutes, about 30 minutes, about 60 minutes, about 90 minutes or about 120 minutes.

When placed in ethanol (either anhydrous or USP), the transdermal patch compositions described herein will release about 0%, about 1%, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100% of the opioid agonist (or prodrug thereof) or agonist-antagonist (or prodrug thereof) from the patch and into the ethanol after about 30 seconds, about 1 minute, about 2 minutes, about 3 minutes, about 4 minutes, about 5 minutes, about 10 minutes, about 15 minutes, about 20 minutes, about 30 minutes, about 60 minutes, about 90 minutes or about 120 minutes.

When placed in ethanol (either anhydrous or USP), the transdermal patch compositions described herein will release about 0%, about 1%, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100% of the opioid antagonist (or prodrug thereof) from the patch and into the ethanol after about 30 seconds, about 1 minute, about 2 minutes, about 3 minutes, about 4 minutes, about 5 minutes, about 10 minutes, about 15 minutes, about 20 minutes, about 30 minutes, about 60 minutes, about 90 minutes or about 120 minutes.

When a transdermal patch composition described herein is placed in ethanol (either anhydrous or USP), the mass to mass ratio (release ratio) of (a) opioid agonist (or prodrug thereof) or opioid agonist-antagonist (or prodrug thereof) in the ethanol to (b) opioid antagonist (or prodrug thereof) in the ethanol will be about 1:60 to about 60:1, such as about 1:60; 1:55; 1:50; 1:45; 1:40; 1:35; 1:30; 1:25; 1:20; 1:15; 1:10; 1:5; 1:4; 1:3; 1:2; 1:1; 2:1; 3:1; 4:1; 5:1; 10:1; 15:1; 20:1; 25:1; 30:1; 35:1; 40:1; 45:1; 50:1; 55:1 and 60:1 after about 30 seconds, about 1 minute, about 2 minutes, about 3 minutes, about 4 minutes, about 5 minutes, about 10 minutes, about 15 minutes, about 20 minutes, about 30 minutes, about 60 minutes, about 90 minutes or about 120 minutes.

In a further embodiment, the release ratio of buprenorphine or a buprenorphine prodrug to naltrexone or a naltrexone prodrug from the pharmaceutical composition, formulation or dosage form (e.g., a transdermal patch) is about 1:1 or less to block the pharmacological effect of the opioid agonist or agonist-antagonist if the composition, formulation or dosage form is misused or abused. In still a further embodiment the release ratio of buprenorphine or a buprenorphine prodrug to naloxone or a naloxone prodrug from the pharmaceutical composition, formulation or dosage form (e.g., a transdermal patch) is about 4:1 or less to block the pharmacological effect of the opioid agonist or agonist-antagonist if the composition, formulation or dosage form is misused.

One embodiment described herein comprises an opioid agonist, opioid agonist-antagonist or a prodrug of the foregoing and an opioid antagonist or a prodrug thereof. The opioid agonist or agonist-antagonist and opioid antagonist or prodrugs of either, as described herein, may be in any form suitable for administration to a mammal, such as in the form of a free base, free acid, salt, ester, hydrate, anhydrate, enantiomer, isomer, tautomer, polymorph, derivative, or the like, provided that the free base, salt, ester, hydrate, enantiomer, isomer, tautomer, or any other pharmacologically suitable derivative is, or becomes, a therapeutically active form of buprenorphine and naltrexone or naloxone.

Further embodiments include a composition of buprenorphine and naltrexone or naloxone, or prodrugs thereof, in any form suitable for transdermal administration to a mammal.

Further embodiments described herein are pharmaceutical compositions comprising: (a) buprenorphine or a prodrug thereof; (b) naltrexone or a prodrug thereof; and (c) a pharmaceutical excipient.

Still further embodiments described herein are pharmaceutical compositions comprising: (a) buprenorphine or a prodrug thereof; (b) naloxone or a prodrug thereof; and (c) a pharmaceutical excipient.

Suitable microneedle arrangements for use with the compounds, compositions, formulations and dosage forms described herein can be found in the foregoing references as well as in U.S. patent application Ser. No. 11/812,249, filed Jun. 15, 2007, published as U.S. 2008 0008745 A1.

Pharmaceutical Excipients

The pharmaceutical compositions described herein can, if desired, include one or more pharmaceutically acceptable excipients. The term "excipient" herein means any substance, not itself a therapeutic agent, used as a carrier or vehicle for delivery of a therapeutic agent to a subject or added to a pharmaceutical composition to improve its handling or storage properties or to permit or facilitate formation of a dose unit of the composition, such as a patch for transdermal or topical delivery. Excipients include, by way of illustration and not limitation, solvents, thickening agents, penetration enhancers, wetting agents, lubricants, emulsifying agents, emollients, substances added to mask or counteract a disagreeable odor, fragrances, antimicrobial preservatives, antioxidants and substances added to improve appearance or texture of the composition. Any such excipients can be used in any dosage forms of the present disclosure. The foregoing list of excipient categories is not meant to be exhaustive but merely illustrative as a person of ordinary skill in the art would recognize that additional excipients could be utilized.

Compositions described herein containing excipients can be prepared by any technique known to a person of ordinary skill in the art of pharmacy, pharmaceutics, drug delivery, pharmacokinetics, medicine or other related discipline that comprises admixing one or more excipients with a therapeutic agent.

In one embodiment, the composition may comprise one or more penetration enhancing agents for transdermal drug delivery. Non-limiting examples of penetration enhancing agents include C8-C22 fatty acids such as isostearic acid, octanoic acid, and oleic acid; C8-C22 fatty alcohols such as oleyl alcohol and lauryl alcohol; lower alkyl esters of C8-C22 fatty acids such as ethyl oleate, isopropyl myristate (IPM), butyl stearate, and methyl laurate; di(lower)alkyl esters of C6-C22 diacids such as diisopropyl adipate; monoglycerides of C8-C22 fatty acids such as glyceryl monolaurate; tetrahydrofurfuryl alcohol polyethylene glycol ether; polyethylene glycol, propylene glycol; 2-(2-ethoxyethoxy)ethanol (transcutol); diethylene glycol monomethyl ether; alkylaryl ethers of polyethylene oxide; polyethylene oxide monomethyl ethers; polyethylene oxide dimethyl ethers; dimethyl sulfoxide; glycerol; ethyl acetate; acetoacetic ester; N-alkylpyrrolidone; and terpenes. Additional penetration enhancers suitable for use can also be found in U.S. patent application Ser. No. 10/032,163, filed Dec. 21, 2001, published as 2002/0111377 A1 and in Thong, et al., "Percutaneous Penetration Enhancers: An Overview," Skin Pharmacology and Physiology, 20:272-828 (2007), which are both hereby incorporated by reference.

The penetration enhancing agent is present in an amount sufficient to provide the desired physical properties and skin penetration profile for the composition. Illustratively, one or more pharmaceutically acceptable penetration enhancer can be present in a total amount by weight of the composition of about 0.1%, about 0.2%, about 0.3%, about 0.4%, about 0.5%, about 1.0%, about 1.5%, about 2.0%, about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, about 10.0%, about 10.5%, about 11.0%, about 11.5%, about 12.0%, about 12.5%, about 13.0%, about 13.5%, about 14.0%, about 14.5%, and or 15.0%. As a further illustration, one or more pharmaceutically acceptable penetration enhancer is present in a total amount by weight between about 0.1% and about 15%; between about 0.1% and about 10%; between about 0.5% and about 10%; or between about 3% and about 8%.

As a further illustration, one or more pharmaceutically acceptable penetration enhancer is present in a total amount by weight between about 1% and about 10%, between about 2% and about 10%, between about 3% and about 10%, between about 4% and about 10%, between about 5% and about 10%, between about 6% and about 10%, between about 7% and about 10%, between about 8% and about 10%, between about 9% and about 10%, between about 1% and about 9%, between about 2% and about 9%, between about 3% and about 9%, between about 4% and about 9%, between about 5% and about 9%, between about 6% and about 9%, between about 7% and about 9%, between about 8% and about 9%, between about 1% and about 8%, between about 2% and about 8%, between about 3% and about 8%, between about 4% and about 8%, between about 5% and about 8%, between about 6% and about 8%, between about 7% and about 8%, between about 1% and about 7%, between about 2% and about 7%, between about 3% and about 7%, between about 4% and about 7%, between about 5% and about 7%, between about 6% and about 7%, between about 1% and about 6%, between about 2% and about 6%, between about 3% and about 6%, between about 4% and about 6%, between about 5% and about 6%, between about 1% and about 5%, between about 2% and about 5%, between about 3% and about 5%, between about 4% and about 5%, between about 1% and about 4%, between about 2% and about 4%, between about 3% and about 4%, between about 1% and about 3%, between about 2% and about 3% and between about 1% and about 2%.

In one embodiment a pressure sensitive adhesive is optionally used to assist in affixing a patch containing an opioid to be transdermally delivered to the subject. In a further embodiment, the pressure sensitive adhesive, or combination of pressure sensitive adhesives, is present in an amount between about 10% and 100%; about 50% and 100%; about 75% and about 100% of the total amount by weight of a layer containing a pressure sensitive adhesive.

Compositions described herein optionally comprise one or more pharmaceutically acceptable wetting agents as excipients. Non-limiting examples of surfactants that can be used as wetting agents in compositions of the disclosure include quaternary ammonium compounds, for example benzalkonium chloride, benzethonium chloride and cetylpyridinium chloride; dioctyl sodium sulfosuccinate; polyoxyethylene alkylphenyl ethers, for example nonoxynol 9, nonoxynol 10, and octoxynol 9; poloxamers (polyoxyethylene and polyoxypropylene block copolymers); polyoxyethylene fatty acid glycerides and oils, for example polyoxyethylene (8) caprylic/capric mono- and diglycerides (e.g., Labrasol™ of Gattefossé), polyoxyethylene (35) castor oil and polyoxyethylene (40) hydrogenated castor oil; polyoxyethylene alkyl ethers, for example polyoxyethylene (20) cetostearyl ether; polyoxyethylene fatty acid esters, for example polyoxyethylene (40) stearate; polyoxyethylene sorbitan esters, for example polysorbate 20 and polysorbate 80 (e.g., Tween™ 80 of ICI); propylene glycol fatty acid esters, for example propylene glycol laurate (e.g., Lauroglycol™ of Gattefossé); sodium lauryl sulfate, fatty acids and salts thereof, for example oleic acid, sodium oleate and triethanolamine oleate; glyceryl fatty acid esters, for example glyceryl monostearate; sorbitan esters, for example sorbitan monolaurate, sorbitan monooleate, sorbitan monopalmitate and sorbitan monostearate; tyloxapol; and mixtures thereof. Such wetting agents, if present, constitute in total about 0.25% to about 15%, about 0.4% to about 10%, or about 0.5% to about 5%, of the total weight of the composition. Illustratively, one or more pharmaceutically acceptable wetting agents are present in a total amount by weight of about 0.25%, about 0.5%, about 0.75%, about 1%, about 1.25%, about 1.5%, about 1.75%, about 2.0%, about 2.25%, about 2.5%, about 2.75%, about 3.0%, about 3.25%, about 3.5%, about 3.75%, about 4.0%, about 4.25%, about 4.5%, about 4.75%, about 5.0%, about 5.25%, about 5.5%, about 5.75%, about 6.0%, about 6.25%, about 6.5%, about 6.75%, about 7.0%, about 7.25%, about 7.5%, about 7.75%, about 8.0%, about 8.25%, about 8.5%, about 8.75%, about 9.0%, about 9.25%, about 9.5%, about 9.75% or about 10%.

Compositions described herein optionally comprise one or more pharmaceutically acceptable lubricants (including antiadherents and/or glidants) as excipients. Suitable lubricants include, either individually or in combination, glyceryl behenate (e.g., Compritol™ 888); stearic acid and salts thereof, including magnesium (magnesium stearate), calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, about 0.2% to about 8%, or about 0.25% to about 5%, of the total weight of the composition. Illustratively, one or more pharmaceutically acceptable lubricants are present in a total amount by weight of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9% or about 10.0%.

In another embodiment, the compositions described herein optionally comprise an emollient. Illustrative emollients include mineral oil, mixtures of mineral oil and lanolin alcohols, cetyl alcohol, cetostearyl alcohol, petrolatum, petrolatum and lanolin alcohols, cetyl esters wax, cholesterol, glycerin, glyceryl monostearate, isopropyl myristate (IPM), isopropyl palmitate, lecithin, allyl caproate, althea officinalis extract, arachidyl alcohol, argobase EUC, butylene glycol, dicaprylate/dicaprate, acacia, allantoin, carrageenan, cetyl dimethicone, cyclomethicone, diethyl succinate, dihydroabietyl behenate, dioctyl adipate, ethyl laurate, ethyl palmitate, ethyl stearate, isoamyl laurate, octanoate, PEG-75, lanolin, sorbitan laurate, walnut oil, wheat germ oil, super refined almond, super refined sesame, super refined soybean, octyl palmitate, caprylic/capric triglyceride and glyceryl cocoate.

An emollient, if present, is present in the compositions described herein in an amount of about 1% to about 30%, about 3% to about 25%, or about 5% to about 15%, by weight. Illustratively, one or more emollients are present in a total amount by weight of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%.

In one embodiment, the compositions described herein comprise an antioxidant. Illustrative antioxidants include citric acid, butylated hydroxytoluene (BHT), ascorbic acid, glutathione, retinol, α-tocopherol, β-carotene, α-carotene, ubiquinone, butylated hydroxyanisole, ethylenediaminetetraacetic acid, selenium, zinc, lignan, uric acid, lipoic acid, and N-acetylcysteine. An antioxidant, if present, is present in the compositions described herein in the amount of less than about 1% by weight. Illustratively, one or more antioxidants are present in the total amount of about 0.025%, about 0.05%, about 0.075%, about 0.1%, 0.125%, about 0.15%, about 0.175%, about 0.2%, 0.225%, about 0.25%, about 0.275%, about 0.3%, 0.325%, about 0.35%, about 0.375%, about 0.4%, 0.425%, about 0.45%, about 0.475%, about 0.5%, 0.525%, about 0.55%, about 0.575%, about 0.6%, 0.625%, about 0.65%, about 0.675%, about 0.7%, 0.725%, about 0.75%, about 0.775%, about 0.8%, 0.825%, about 0.85%, about 0.875%, about 0.9%, 0.925%, about 0.95%, about 0.975%, or about 1.0%, by weight. As a further illustration one or more antioxidants are present in the total amount by weight of between about 0.01% and about 1.0%; about 0.05% and about 0.5% or about 0.05% and about 0.2%.

In one embodiment, the compositions described herein comprise an antimicrobial preservative. Illustrative anti-microbial preservatives include acids, including but not limited to benzoic acid, phenolic acid, sorbic acids, alcohols, benzethonium chloride, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, propylparaben, sodium propionate, or thimerosal. The anti-microbial preservative, if present, is present in an amount of about 0.1% to about 5%, about 0.2% to about 3%, or about 0.3% to about 2%, by weight, for example about 0.2%, about 0.4%, about 0.6%, about 0.8%, about 1%, about 1.2%, about 1.4%, about 1.6%, about 1.8%, about 2%, about 2.2%, about 2.4%, about 2.6%, about 2.8%, about 3.0%, about 3.2%, about 3.4%, about 3.6%, about 3.8%, about 4%, about 4.2%, about 4.4%, about 4.6%, about 4.8%, or about 5% by weight.

Compositions described herein optionally compromise one or more emulsifying agents. The term "emulsifying agent" refers to an agent capable of lowering surface tension between a non-polar and polar phase and includes compounds defined elsewhere as "self emulsifying" agents. Suitable emulsifying agents can come from any class of pharmaceutically acceptable emulsifying agents including carbohydrates, proteins, high molecular weight alcohols, wetting agents, waxes and finely divided solids. The optional emulsifying agent may be present in the composition in a total amount of about 1% to about 25%, about 1% to about 20%, about 1% to about 15%, or about 1% to about 10% by weight of the composition. Illustratively, one or more emulsifying agents are present in a total amount by weight of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25%.

In another embodiment, propylene glycol is present in a composition in an amount of about 1% to about 99%, by weight of the composition, for example about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 99%.

Composition described herein may optionally comprise one or more alcohols. In a further embodiment, the alcohol is a lower alcohol. As used herein, the term "lower alcohol," alone or in combination, means a straight-chain or branched-chain alcohol moiety containing one to six carbon atoms. In one embodiment, the lower alcohol contains one to four carbon atoms, and in another embodiment the lower alcohol contains two or three carbon atoms. Examples of such alcohol moieties include ethanol, ethanol USP (i.e., 95% v/v), n-propanol, isopropanol, n-butanol, isobutanol, sec-butanol, and tert-butanol. As used herein, the term "ethanol" refers to $C_2H_5OH$. It may be used as dehydrated alcohol USP, alcohol USP or in any common form including in combination with various amounts of water. If present, the alcohol is present in an amount sufficient to form a composition which is suitable for contact with a mammal. Illustratively, one or more pharmaceutically acceptable alcohol is present in a total amount by weight of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 98%. As a further illustration, one or more pharmaceutically acceptable alcohol is present in a total amount by weight between about 1% and about 98%; between about 10% and about 95%; between about 25% and about 75%; between about 35% and about 70%; or between about 40% and about 50%.

In a further embodiment, the pharmaceutical composition is substantially free of water. In yet a further embodiment, the pharmaceutical composition is anhydrous.

Combination with Non-Opioid Agents

In one embodiment, the pharmaceutical composition containing the opioid can also be combined with an optional second non-opioid pharmacologically active agent for the treatment of pain and/or polydrug abuse, including, for example, a cannabinoid (agonist, antagonist, or inverse agonist), bupropion, hydroxybupropion, nicotine, nornicotine, varenicline, doxepin, acetaminophen, aspirin, diclofenac or another non-steroidal anti-inflammatory drug. The cannabinoid could consist of one or more of the drugs or prodrugs as described in U.S. patent application Ser. No. 11/157,034, filed Jun. 20, 2005, published as U.S. 2005/0266061 A1, U.S. patent application Ser. No. 12/182,974, filed Jul. 30, 2008, published as U.S. 2009/036523 A1 and U.S. patent application Ser. No. 12/326,036, filed Dec. 1, 2008, published as U.S. 2009/0143462. The previous listing of suitable compounds for use as an optional second non-opioid pharmacologically active agent is not meant to be exhaustive, as a person of ordinary skill in the art would understand that other compounds (such as those found in the Merck Index, Thirteenth Edition and the Physicians Desk Reference, 58$^{th}$ ed.) would be suitable for use as the optional second non-opioid pharmacologically active agent in the invention disclosed herein. These opioid agonists and/or agonist-antagonists like buprenorphine could also be combined with a second drug for the treatment of pain and/or polydrug abuse, such as a cannabinoid. The cannabinoid could consist of one or more of the foregoing drugs or prodrugs as described in previous patent applications.

Therapeutic Uses

Methods of treating one or more medical conditions such as opioid dependence, alcohol dependence, polydrug addiction, pain, cocaine addiction, eating disorders (e.g., binge eating) and treatment-resistant depression are described herein and comprise transdermally administering an opioid from an abuse-resistant formulation. In one embodiment, compositions described herein which are transdermally administrable include opioid agonists or agonist-antagonists, such as buprenorphine, and opioid antagonists, such as naltrexone and/or naloxone.

In another embodiment, compositions described herein which are transdermally administrable include opioid agonists or agonist-antagonists, such as buprenorphine, and prodrugs of opioid antagonists, such as prodrugs of naltrexone and/or naloxone.

In another embodiment, compositions described herein which are transdermally administrable include prodrugs of opioid agonists or agonist-antagonists, such as prodrugs of buprenorphine, and opioid antagonist prodrugs, such as prodrugs of naltrexone and/or naloxone.

In another embodiment, compositions described herein which are transdermally administrable include prodrugs of opioid agonists or agonist-antagonists, such as prodrugs of buprenorphine, and opioid antagonist, such as naltrexone and/or naloxone.

In another embodiment, compositions disclosed herein comprise one or more opioid agonists or agonist-antagonists, including buprenorphine, in a total amount of about of between about 0.1% and about 95% by weight of the composition. For example, one or more opioid agonists or agonist-antagonists may be present in the amount by weight of: about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 4%, about 5%, about 6%, about 7%, about 8%, about 9%, about 10%, about 11%, about 12%, about 13%, about 14%, about 15%, about 20%, about 25%, about 30%, about 35%, about 40%, about 45%, about 50%, about 55%, about 60%, about 65%, about 70%, about 75%, about 80%, about 85%, about 90% or about 95%.

In another embodiment, compositions disclosed herein comprise one or more prodrugs of opioid agonists or agonist-antagonists, including prodrugs of buprenorphine, in a total amount of about of between about 0.1% and about 95% by weight of the composition. For example, one or more opioid agonists or agonist-antagonists may be present in the amount by weight of: about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 4%, about 5%, about 6%, about 7%, about 8%, about 9%, about 10%, about 11%, about 12%, about 13%, about 14%, about 15%, about 20%, about 25%, about 30%, about 35%, about 40%, about 45%, about 50%, about 55%, about 60%, about 65%, about 70%, about 75%, about 80%, about 85%, about 90% or about 95%.

In another embodiment, compositions disclosed herein comprise one or more opioid antagonists, including naltrexone and/or naloxone, in a total amount of about of between about 0.1% and about 95% by weight of the composition. For example, one or more opioid antagonists may be present in an amount by weight of: about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 4%, about 5%, about 6%, about 7%, about 8%, about 9%, about 10%, about 11%, about 12%, about 13%, about 14%, about 15%, about 20%, about 25%, about 30%, about 35%, about 40%, about 45%, about 50%, about 55%, about 60%, about 65%, about 70%, about 75%, about 80%, about 85%, about 90% or about 95%.

In another embodiment, compositions disclosed herein comprise one or more opioid antagonist prodrugs, including prodrugs of naltrexone and/or prodrugs of naloxone, in a total amount of about of between about 0.1% and about 95% by weight of the composition. For example, one or more opioid agonists or agonist-antagonists may be present in the amount by weight of: about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 4%, about 5%, about 6%, about 7%, about 8%, about 9%, about 10%, about 11%, about 12%, about 13%, about 14%, about 15%, about 20%, about 25%, about 30%, about 35%, about 40%, about 45%, about 50%, about 55%, about 60%, about 65%, about 70%, about 75%, about 80%, about 85%, about 90% or about 95%.

The compositions described herein are used in a "pharmacologically effective amount." This means that the rate and extent of absorption of the active by the subject is such that it results in a therapeutic level of the active in the subject over the period that such compound is to be used. Such delivery is dependent on a number of variables including the time period for which the individual dosage unit is to be used, the flux rate of the active from the composition into the subject, for example, buprenorphine or a buprenorphine prodrug, from the formulation, surface area of the application site, etc.

In another embodiment, a single dosage unit comprises a therapeutically effective amount or a therapeutically and/or prophylactically effective amount of an opioid such as buprenorphine or prodrugs of buprenorphine. The term "therapeutically effective amount" or "therapeutically and/or prophylactically effective amount" as used herein refers to an amount of opioid that is sufficient to elicit the required or desired therapeutic and/or prophylactic response, as the particular treatment context may require. Single dosage unit as used herein includes individual patches. In one embodiment, a single dosage unit of any formulation comprises a therapeutically effective amount or a therapeutically and/or prophylactically effective amount of buprenorphine or a buprenorphine prodrug.

It will be understood that a therapeutically and/or prophylactically effective amount of an opioid for a subject is dependent inter alia on the body weight of the subject as well as other factors known to a person of ordinary skill in the art. A "subject" herein to which a therapeutic agent or composition thereof can be administered includes mammals such as a human of either sex and of any age, and also includes any nonhuman animal, particularly a domestic, farm or companion animal, illustratively, a cat, cow, pig, dog or a horse as well as laboratory animals such as guinea pigs and primates.

In one embodiment, compositions described herein are suitable for transdermal administration. In another embodiment, transdermally administrable compositions are adapted for administration to the abdomen, back, chest, legs, arms, scalp or other suitable skin surface.

The terms "treat", "treated", "treating" and "treatment" are to be broadly understood as referring to any response to, or anticipation of, a medical condition in a mammal, particularly a human, and includes but is not limited to:
 (i) inhibiting the medical condition, i.e., arresting, slowing or delaying the on-set, development or progression of the medical condition; or
 (ii) relieving the medical condition, i.e., causing regression of the medical condition.

In one embodiment, a therapeutically effective amount of an opioid, such as buprenorphine, is administered transdermally in an abuse-resistant or abuse deterrent formulation to treat a medical condition selected from the group consisting of: opioid dependence, alcohol dependence, polydrug addiction, pain, cocaine addiction, eating disorders (e.g., binge eating) and treatment-resistant depression.

Pain can include nociceptive pain, such as somatic pain and visceral pain, and non-nociceptive pain, such as neuropathic pain, sympathetic pain, psychogenic pain and idiopathic pain. Pain also include chronic and acute pain. Non-limiting examples of pain or sources of pain include fibromyalgia, chronic back pain (both deep and superficial somatic pain), chronic pancreatitis, chronic acute hepatitis, gallstone, appendicitis, post-herpetic neuralgia, trigeminal neuralgia, phantom limb pain, diabetic neuropathy, carpal tunnel syndrome, sciatica, pudendal neuralgia, central pain syndrome, spinal cord injury, post-surgical pain, cancer, degenerative disk disease, osteoporosis, peripheral neuropathy, herpes zoster (shingles), lupus, reflex sympathetic dystrophy, headaches (migraines, tension and cluster), temporomandibular disorders, such as temporomandibular joint syndrome, myofacial pain and internal derangement of the joint and degenerative joint disease, such as osteoarthritis and rheumatoid arthritis.

Eating disorders can include anorexia nervosa, bulimia nervosa, binge eating disorder (BED), compulsive overeating, purging disorder, rumination, diabulimia, food maintenance, eating disorders not otherwise specified (EDNOS), pica, night eating syndrome and orthorexia nervosa.

In one embodiment, the pharmaceutical composition comprising an opioid, such as buprenorphine, is administered once daily to a subject in need thereof. In a further embodiment, the pharmaceutical composition comprising an opioid, such as buprenorphine, is administered twice daily to a subject in need thereof. In a further embodiment, the pharmaceutical composition comprising an opioid, such as buprenorphine, is administered more than twice daily, such as three, four, five, six, seven or eight times daily.

In a further embodiment, the pharmaceutical composition is administered every second day, every third day, every fourth day, every fifth, every sixth day, or once weekly.

In another illustrative embodiment, a transdermal patch can be one which is capable of controlling the release of the opioid agonists or agonist-antagonists or prodrugs of the foregoing such that transdermal delivery of the active compound is substantially uniform and sustained over a period of about 6 hours, about 12 hours, about 24 hours, about 48 hours or about 7 days. Such transdermal patch which can be used in the practice of the methods described herein can take the form of an occlusive body having a backing layer. In practice, the occlusive body which includes the opioid agonists or agonist-antagonists or prodrugs of the foregoing is positioned on the subject's skin under conditions suitable for transdermally delivering the active compound to the subject Pharmaceutical Dosage Forms In one embodiment, a first transdermal dosage form, comprising an opioid agonist, an opioid agonist prodrug, an opioid agonist-antagonist or an opioid agonist-antagonist prodrug and an opioid antagonist or an opioid antagonist prodrug, is administered to a subject. In a further embodiment, the first transdermal dosage form is a patch which is administered to the subject one time after which it is discarded. Following the single administration of the first transdermal dosage form, the systemic concentration of the opioid agonist or opioid agonist-antagonist can be measured over time and the maximum concentration ("Cmax"), time to maximum concentration ("Tmax") after administration and area under the time versus blood plasma or serum concentration curve ("AUC") can be calculated therefrom. In such an embodiment, AUC can be calculated from 0 to 24 hours or from 0 hours to infinity. In a further embodiment, the transdermal dosage form is administered multiple times to the subject, until the opioid agonist or the opioid agonist-antagonist achieves a steady-state systemic concentration. After steady-state has been achieved, the systemic concentration of the opioid agonist or the agonist-antagonist can be measured over time, and a maximum steady state concentration ("Cmax-ss") and minimum steady state concentration ("Cmin-ss") of the opioid agonist or the agonist-antagonist can be determined.

In one embodiment, a second transdermal dosage form, comprising the same opioid agonist, an opioid agonist prodrug, an opioid agonist-antagonist or an opioid agonist-antagonist prodrug and an opioid antagonist or an opioid antagonist prodrug of the prior transdermal dosage form, is administered to a subject. In a further embodiment, the second transdermal dosage form satisfies the regulatory requirements for bioequivalence to the prior transdermal dosage form.

In a further embodiment, the second transdermal dosage form is administered to the subject one time after which it is discarded. In a further embodiment, the systemic concentration of the opioid agonist or the opioid agonist-antagonist resulting from administration of the second transdermal dosage form is measured over time and the Cmax, Tmax and AUC resulting from the administration of the second transdermal dosage form is measured. In such an embodiment, AUC can be calculated from 0 to 24 hours or from 0 hours to infinity. In a further embodiment, the Cmax, Tmax and AUC of the opioid agonist or the opioid agonist-antagonist from the second transdermal dosage form is between about 60% and 140% of the Cmax, Tmax and AUC of the opioid agonist or the opioid agonist-antagonist from the first dosage form. In a further embodiment, the Cmax, Tmax and AUC of the opioid agonist or the opioid agonist-antagonist from the second transdermal dosage form is between about 80% and 125% of the Cmax, Tmax and AUC of the opioid agonist or the opioid agonist-antagonist from the first dosage form.

In an additional embodiment, the second transdermal dosage form is administered multiple times to the subject, until the opioid agonist or the opioid antagonist achieves a steady state systemic concentration. In a further embodiment, after steady-state has been achieved, the systemic concentration of the opioid agonist or the agonist-antagonist from the second transdermal dosage form can be measured over time, and Cmax-ss and Cmin-ss of the opioid agonist or the agonist-antagonist can be determined. In a further embodiment, the Cmax-ss and Cmin-ss of the opioid agonist or the opioid agonist-antagonist from the second transdermal dosage form is between about 60% and 140% of the Cmax-ss and Cmin-ss of the opioid agonist or the opioid agonist-antagonist from the first dosage form. In further embodiment, the Cmax-ss and Cmin-ss of the opioid agonist or the opioid agonist-antagonist from the second transdermal dosage form is between about 80% and 125% of the Cmax-ss and Cmin-ss of the opioid agonist or the opioid agonist-antagonist from the first dosage form.

Patch Formulations

The compounds and pharmaceutical compositions described herein are suitable for use in transdermal delivery devices such as patches and the like. For example, the compounds and compositions described herein are suitable for use in a membrane-modulated transdermal delivery system. In this system, the reservoir containing the compound to be transdermally administered to the patient is encapsulated in a shallow compartment molded from a drug impermeable backing and a rate controlling polymeric membrane through which the compound to be delivered in a controlled manner. In one embodiment, the external surface of the membrane has a thin layer of a drug-compatible, hypoallergenic adhesive polymer (e.g., silicone or polyacrylate adhesive) which is applied to achieve intimate contact of the transdermal system with the skin.

The compounds and pharmaceutical compositions described herein are also suitable for use in adhesive-diffusion controlled transdermal systems. In these embodiments, the drug (e.g., one or more opioids) reservoir is formulated by directly dispersing the drug (or drugs) to be delivered in an adhesive polymer and then spreading the drug-loaded adhesive onto a flat sheet of a drug-impermeable backing membrane or backing layer to form a thin drug reservoir layer having a thickness of between about 0.1 mil and about 100 mil, such as about 1 mil to about 40 mil and about 30 mil to about 40 mil. Optionally, on top of the drug reservoir layer, additional layers of non-medicated rate controlling adhesive polymer of constant thickness are placed to produce an adhesive diffusion-controlled drug-delivery system. Also, optionally a second adhesive layer can be added which can contain a drug substance whether or not it is to be transdermally delivered to the subject.

The compounds and pharmaceutical compositions described herein are also suitable for use in matrix dispersion-type systems. In these systems, the drug reservoir is formed by homogeneously dispersing the drugs in a hydrophilic or lipophilic polymer matrix, and the medicated polymer then is molded into a medicated disc with a defined surface area and controlled thickness. The disc then is glued onto an occlusive baseplate in a compartment fabricated from a drug-impermeable backing. The adhesive polymer is spread along the circumference to form a strip of adhesive rim around the medicated disc.

The compounds and pharmaceutical compositions described herein are also suitable for use in microreservoir systems. In these systems, the drug reservoir is formed by first suspending the drug particles in an aqueous solution of water-soluble polymer and then dispersing it homogeneously in a lipophilic polymer by high-shear mechanical force to form a large number of unleachable, microscopic spheres of drug reservoirs. This unstable dispersion is quickly stabilized by immediately cross-linking, which produces a medicated polymer disc with a constant surface area and fixed thickness. A transdermal therapeutic system is produced in which the medicated disc is positioned at the center and surrounded by an adhesive rim.

In any of the foregoing, the transdermal delivery systems may optionally comprise one or more layers, whether containing an opioid or not, rate controlling, non-rate controlling, a barrier layer and/or a rate-controlling membrane film.

Patch formulations can be optimized using in vitro human skin diffusion testing prior to the selection of a limited number of patch formulations or patch compositions for stability testing. In one embodiment, the drug and adhesive are formulated into one monolithic layer. The drug can be mixed with an adhesive (e.g. silicone type, available from Dow Corning and other manufacturers) in a solvent (e.g. ethyl acetate). This drug mixture would then be extruded onto a polyester backing film to a uniform thickness of, for example, about 100 microns or greater with a precision wet film applicator. The solvent is allowed to evaporate in a drying oven and the resulting "patch" is trimmed to fit the diffusion cell donor chamber. Various patch formulations can be made until the desired steady-state flux rate and adhesive properties are obtained. Different adhesives can be tried, as well as varying the amount of adhesive in the formulation (Nalluri, Milligan et al. 2005). Suitable results have been obtained by making monolithic patches with DURO-TAK 387-2051, which is an acrylate-vinyl acetate non-curing pressure sensitive adhesive from the National Starch Chemical Company. Different solvents (e.g. isopropyl myristate, propylene glycol) can optionally be incorporated into the formulation in an attempt to optimize the delivery rate. Other transdermal patch embodiments may optionally include multiple layers of adhesive, multiple layers of opioid agonist, opioid agonist-antagonist or prodrugs of the foregoing multiple layers of opioid antagonist or opioid antagonist prodrugs and multiple barrier layers.

In a further embodiment, reservoir patches can be made if it appears, for example, that the drugs are not compatible with a monolithic matrix patch formulation. In the reservoir system, the active ingredient(s) and any excipient(s) could be formulated into a gel and sealed between a release layer and an impermeable backing material such as polyester or other suitable material known to a person of skill in the art. Ethyl vinyl acetate membranes with acrylic adhesives have been found to be suitable.

Adhesive patch formulations can be prepared containing different loadings of an opioid agonists or agonist-antagonists or prodrugs of the foregoing by using DURO-TAK adhesives (National Starch and Chemical Company, USA). Appropriate amounts of adhesive and drug can be sonicated for ten minutes, cast onto the release liner (9742 Scotchpak, 3M, St. Paul, Minn.) with a wet film applicator (Paul N. Gardner Company, Inc., Pompano Beach, Fla.) set at a 40 mil thickness, and kept at room temperature for one hour and then at 70° C. in an oven for ten minutes (to remove any residual solvent). The patches would then be covered with backing membrane (CoTran 9722, 3M, St. Paul, Minn.), cut into appropriate sizes, and then can be stored in a desiccator for further study.

In further embodiments, additional adhesives which are suitable for preparing patch formulations and transdermal delivery devices such as patches include polyisobutylenes, acrylates, silicone and combinations of the foregoing. Additional adhesives can be found in U.S. patent application Ser. No. 11/907,954, filed Oct. 18, 2007, published as U.S. 2009/017102 A1.

In a further embodiment, the transdermal patch may optionally comprise one or more than one layer of opioid agonist, opioid agonist-antagonist or opioid antagonist or a prodrug of any of the foregoing. In a further embodiment, a respective layer may comprise an opioid agonist or an opioid agonist-antagonist alone or, optionally, in combination with an opioid antagonist. In yet a further embodiment, a respective layer may comprise an opioid antagonist separate from a layer comprising an opioid agonist or an opioid agonist-antagonist.

In a further embodiment, one or more buprenorphine prodrugs can be used with or instead of buprenorphine in the pharmaceutical compositions and patches described herein. In an additional embodiment, a buprenorphine prodrug can be used with or instead of buprenorphine in the method of administering buprenorphine to a mammal as described herein. In a further embodiment, a buprenorphine prodrug can be used with or instead of buprenorphine in the method of treating a medical condition by the administration of buprenorphine described herein, wherein the medical conditions is selected from the group consisting of: opioid dependence, alcohol dependence, polydrug addiction, pain, cocaine addiction, eating disorders (e.g., binge eating) and treatment-resistant depression.

Spray Formulation

In another embodiment, the opioid agonist (or prodrug thereof) or opioid agonist-antagonist (or prodrug thereof) can be delivered transdermal with a spray system. The metered dose spray would dispense a therapeutically effective dose to the skin. The dosing level could be achieved by creating a spray system that covers a desired skin area. The opioid agonist (or prodrug thereof) or opioid agonist-antagonist (or prodrug thereof) would absorb into the skin, forming a depot within the horny layer of this skin, and provide a sustained delivery of the opioid agonist (or prodrug thereof) or opioid agonist-antagonist (or prodrug thereof). In further embodiments, the metered dose spray may contain alcohols, fragrance, chemical enhancers (penetration enhancers), plasticizers, emollients, water, thickening agents, pH modifiers, fillers and preservatives as well as other suitable excipients.

EXAMPLES

Example 1

Several patch formulations were made by the methods described herein. The bi-layer patch formulations contained a naltrexone (NTX) or naloxone (NLX) layer incorporating ethylcellulose (EC)/hydroxypropylcellulose (HPC) polymer, an EC/HPC polymeric film and a buprenorphine or buprenorphine prodrug (ALL00160) layer. The buprenorphine prodrug ALL00160 has the following structure:

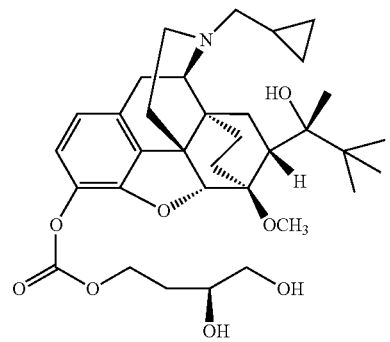 [SMILES: CO[C@]12CC[C@@]3(C[C@@H]1[C@](C)(O)C(C)(C)C)[C@H]1Cc4ccc(OC(=O)OCC[C@H](O)CO)c5c4[C@@]3(CCN1CC1CC1)[C@H]2O5]

The synthesis of ALL00160 can be found in U.S. patent application Ser. No. 13/079,744 filed on 04/04/2011 which claims priority to U.S. Provisional Patent Application 61/320,514, filed Apr. 2, 2010 and U.S. Provisional Application Ser. No. 61/320,522, filed Apr. 2, 2010.

No antagonist was detected in the skin or in the receiver solution after in vitro skin diffusion testing.

The mass ratio of drug release from the transdermal patch formulation needed under abuse conditions is 4:1 for BUP:NLX to mimic the naloxone/buprenorphine sublingual tablet ratio, however this ratio needs to be 1:1 for BUP:NTX since naltrexone is a less potent opioid antagonist than NLX. A total of 1-5 mg of naltrexone HCl per Embeda® (Pfizer/King Pharmaceuticals) tablet is sufficient to prevent abuse via buccal absorption or injection. The ratios here are optimized based on the higher potency of buprenorphine than morphine (Embeda). It is also acceptable if the ratios for BUP:NLX are less than 4:1, or less than 1:1 for BUP:NTX, as this means more antagonist is available to block the agonist effects of BUP. In order to simulate three different abuse scenarios, release of the buprenorphine prodrug (ALL00160) from abuse-deterrent patches was studied in ethanol, water and pH 6.5 phosphate buffer. Ethanol and water would be typical solvents that drug abusers would use to dissolve the patch contents in order to inject the opiate for attainment of a rapid high. The pH 6.5 phosphate buffer simulates the buccal abuse scenario where the patch is chewed to release opiate quickly so that it is absorbed from the buccal cavity.

In the patch release studies, the improved release ratio of buprenorphine:NLX in ethanol was 1.3-1.8:1 (required ratio to observe narcotic blockade is 4:1 or less). Similar results were also observed for naltrexone with release ratio of 0.5:1 in ethanol after 30 min (required ratio is 1:1 or less). Similarly, the release ratio of both NLX and NTX in water was in the required range.

In the laboratory chewing simulation studies (phosphate buffer, pH 6.5), the release ratio of buprenorphine:NLX was about 0.3:1 within 5 min and 0.8-1.0:1 for buprenorphine:NTX after 3 min.

Preparation of Opioid Antagonist Layer

HPC and EC were employed in the preparation of this layer. HPC polymer solution was prepared by dissolving 15% of polymer (Klucel®-EF, Hercules, Wilmington, Del.) in ethanol. 15% EC solution was made by dissolving polymer (N50, Hercules, Wilmington, Del.) in chloroform-methanol (8:2). Both polymer solutions were mixed together in a combination of 1:9 (HPC:EC) on a total polymer content basis.

The opioid antagonist layer comprising naltrexone hydrochloride (10% or 15%) or naloxone hydrochloride (10%) and 20% of EC/HPC polymer mixture by dry weight of the patch was made by mixing the opioid antagonist and EC/HPC polymer solution with DURO-TAK® adhesive 87-900A (National Starch and Chemical Company, USA) by vortex and sonication for approximately 15 min.

The opioid antagonist layer comprised of naltrexone hydrochloride (13%) and 20% of EC/HPC polymer mixture by dry weight of the patch was made by mixing the opioid antagonist and EC/HPC polymer solution with 60% BIO-PSA 7-4302 and 40% BIO-PSA 7-4202 (Dow Corning®, Midland, Mich.) by vortex and sonication for approximately 15 min.

On a film coater (EC-20, ChemInstruments Inc., Fairfield, Ohio), the formulations were cast onto a release liner (1022 ScotchPak™, 3M™, St. Paul, Minn.) with a wet film applicator (Paul N. Gardner Company Inc., Pompano Beach, Fla.) set at 20 mil thickness. The cast film was then dried at room temperature in the fume hood for 30 min and then at 65-70° C. in an oven for 12-15 min to remove any residual solvent. The patch was then covered with a backing film (1109 Scotch-Pak™, 3M™, St. Paul, Minn.) and stored in a desiccant cabinet for further laminating with the other layers.

Polymeric Film

A rate-controlling EC membrane incorporated with a water-soluble HPC polymer was prepared and evaluated for the abuse-resistant transdermal delivery system. 15% (w/v) EC dissolved in chloroform-methanol (8:2) and 15% (w/v) HPC dissolved in ethanol were used to prepare the polymeric film. Polyethylene glycol 400 at 40% w/w of the polymer was used as a plasticizer. 80% of EC and 20% of HPC by weight of the composition were mixed together with the plasticizer by vortex and sonication for about 15 min. The mixture was then cast onto the 1022 ScotchPak™ release liner with a wet film applicator set at 20 mil thickness. The cast film was dried overnight in a fume hood at room temperature. The dried film was stored in a desiccant cabinet for further laminating with an opioid agonist layer and an opioid antagonist layer to form a transdermal patch.

Patch Lamination

Opioid antagonist layer loaded with naloxone hydrochloride (10%) or naltrexone hydrochloride (10%, 13% or 15%) was laminated with the EC/HPC polymeric film and the opioid agonist-antagonist layer (which was loaded with 5% or 7% buprenorphine prodrug or 5% buprenorphine). The polymeric film was placed between opioid antagonist layer and opioid agonist or agonist-antagonist (or prodrug of either an opioid agonist or opioid agonist-antagonist) (FIG. 1). For the 13% NTX-EC/HPC, 5% BUP-F1 patch, the opioid agonist-antagonist layer comprised the buprenorphine formulation. For the 13% NTX-EC/HPC, 5% BUP-F2, the opioid agonist-antagonist layer comprised the buprenorphine prodrug formulation. An extra layer of adhesive (Acrylic 87-900A, 5 mil thickness) was used in the formulation of 15% NTX-EC/HPC, 5% BUP PD patch which was adhered to the 15% NTX-EC/HPC layer. The thickness of the 5% BUP PD layer was 15 mil compared to the 20 mil thickness used for the opioid agonist-antagonist layer in the patch formulations.

Patch Release Study

In vitro patch release studies were performed in ethanol and in water to observe the release profiles of naloxone/naltrexone and buprenorphine/buprenorphine prodrug. Briefly, a patch was cut into 1 cm$^2$ and placed into 5 mL ethanol or water and the drug release was carried out on a shaker for 30 min or 2 h. 100 μL of sample was withdrawn at predetermined time intervals and diluted into 900 μL acetonitrile for HPLC analysis. The results are summarized in Tables 2, 5, 8, 11, 14, 17 and 20 (ethanol) and Tables 3, 6, 9, 12, 15, and 18 (water).

In Vitro Simulation of Patch Abuse by Chewing

To simulate abuse of buprenorphine by chewing/squeezing the drug from the patch, a 1 cm$^2$ patch was placed into 2 mL of 0.1 M phosphate buffer (pH 6.5). A Teflon stick was used to press, squeeze and poke the patch against the inside wall of a scintillation vial for 5 min. 200 μL of sample was taken at predetermined time intervals and mixed with 800 μL acetonitrile for HPLC analysis. The ratio of total buprenorphine and naloxone/naltrexone was calculated and summarized in Tables 4, 7, 10, 13, 16 and 19.

Analytical Method

| | |
|---|---|
| Column | Brownlee ® C$_{18}$ reversed phase Spheri 5 μm, (4.6 × 220 mm) column with a Brownlee ® C$_{18}$ reversed phase 7 μm (3.2 × 150 mm) guard column |
| Mobile phase | 90:10 acetonitrile: 0.1% trifluoroacetic acid with 5% acetonitrile, pH = 3 with triethylamine |
| Flow rate | 1.5 mL/min |
| Wavelength | 210 nm |
| Injection volume | 100 μL (diffusion samples and respective standards) 20 μL (skin samples, patch samples, and respective standards) |
| Run time | 5 min |
| Retention times | naltrexone = 3 min<br>naloxone = 3 min<br>ALL00160 = 3.6 min<br>buprenorphine = 4.2 min |
| Naltrexone (skin) | LOD in acetonitrile standards is 0.173 μg/mL or 0.507 nmol/mL<br>LOD for skin samples = 17.3 ng NTX/mg of skin |
| Naloxone (skin) | LOD in ACN standards is 0.107 μg/mL or 0.327 nmol/mL<br>LOD for skin samples = 10.7 ng NLX/mg of skin |
| Naltrexone (receiver fluid) | 0.0346 μg/mL |
| Naloxone (receiver fluid) | 0.0215 μg/mL |

Data Analysis

Cumulative quantity of drug collected in the receiver compartment was plotted as a function of time. The flux value for a given experiment was obtained from the slope of a steady state portion of the cumulative amount of drug permeated vs. time plot. Lag time was obtained from the x-intercept of the steady state portion of the cumulative amount of drug permeated vs. time plot. These values represent the data as total buprenorphine equivalents delivered in the form of buprenorphine and/or prodrug.

Results

In vitro diffusion studies were monitored for 72 h. The permeation parameters of formulations comprising naltrexone ([13% NTX-EC/HPC, 5% BUP PD], [15% NTX-EC/HPC, 5% BUP PD-15 mil and 20 mil], [10% NTX-EC/HPC film, 7% BUP PD] and [13% NTX EC/HPC film, 5% BUP]) and naloxone (10% NLX-EC/HPC film, 7% BUP PD), including flux values, lag time, drug amount in skin and cumulative amount, are summarized in Table 1. No detectable levels of NTX or NLX were found in the diffusion samples or skin samples except in the 15% NTX-EC/HPC, 5% BUP PD-20 mil patch. NTX had limited diffusion from the 15% NTX over the 20 mil BUP PD layer. This level of permeation is non therapeutically significant and therefore should not interfere with opiate therapy. Likewise, the skin content was very low suggesting a low exposure to the opioid antagonist.

The results of in vitro drug release from the patch in ethanol and water are presented in Tables 2, 5, 8, 11, 14, 17 and 20 (ethanol) and Tables 3, 6, 9, 12, 15, and 18 (water). The results of chewing simulation test are presented in Tables 4, 7, 10, 13, 16 and 19. Due to limited patch material for the 13% NTX-EC/HPC, 5% BUP-F2, no patch testing was conducted in water or 0.1 M phosphate buffer.

Tables

TABLE 1

Permeation parameters of naltrexone/naloxone through human skin in vitro from patch

| Patch | Flux (nmol/cm²/h) | Lag time (h) | Drug in skin (μmol/g) | Cumulative amount (nmol) | n |
|---|---|---|---|---|---|
| Naltrexone and Buprenorphine prodrug | | | | | |
| 15% NTX-EC/HPC film, 5% BUP PD-15 mil | 0 | ND* | 0 | 0 | 2 |
| 15% NTX-EC/HPC film, 5% BUP PD-20 mil | 0.06 ± 0.003 | 40.75 ± 10.45 | 0.04 ± 0.05 | 3.86 ± 1.85 | 4 |
| 10% NTX-EC/HPC film, 7% BUP PD | 0 | ND | 0 | 0 | 3 |
| Naloxone and Buprenorphine prodrug | | | | | |
| 10% NLX-EC/HPC film, 7% BUP PD | 0 | ND | 0 | 0 | 3 |
| Naltrexone and Buprenorphine formulation | | | | | |
| 13% NTX-EC/HPC film, 5% BUP-F1 | 0 | ND | NA** | 0 | 4 |
| 13% NTX-EC/HPC film, 5% BUP-F2 | 0 | ND | NA | 0 | 4 |

*ND = not determined;
**NA = not available

13% Naltrexone-EC/HPC film, 5% Buprenorphine prodrug

TABLE 2

Release ratio of total buprenorphine:naltrexone from patch (13% NTX-EC/HPC film, 5% BUP PD) in ethanol (see also FIG. 5)

| Time (min) | Ratio in ethanol (total BUP:NTX) | NTX in ethanol (mg/cm²) | BUP in ethanol (mg/cm²) |
|---|---|---|---|
| 5 | 7.60 | 0.10 | 0.79 |
| 10 | 3.80 | 0.23 | 0.87 |
| 15 | 0.94 | 0.91 | 0.85 |
| 30 | 0.80 | 1.16 | 0.93 |

Release ratio of total buprenorphine:naltrexone from patch (13% NTX-EC/HPC film, 5% BUP PD) in ethanol

| Time (min) | Amount of BUP released (μg) | Percentage of BUP released (%) | Amount of NTX released (μg) | Percentage of NTX released (%) | Ratio in ethanol (total BUP:NTX) |
|---|---|---|---|---|---|
| 5 | 394.3 | 56.3 | 51.9 | 10.4 | 7.60 |
| 10 | 433.5 | 61.2 | 114.1 | 22.8 | 3.80 |
| 15 | 424.9 | 60.7 | 452.8 | 90.6 | 0.94 |
| 30 | 463.2 | 66.2 | 578.0 | 100 | 0.80 |

TABLE 3

Release ratio of total buprenorphine:naltrexone from patch (13% NTX-EC/HPC film, 5% BUP PD) in water (see also FIG. 6)

| Time (min) | Ratio in water (total BUP:NTX) | NTX in water (mg/cm²) | BUP in water (mg/cm²) |
|---|---|---|---|
| 5 | 0.13 | 0.26 | 0.034 |
| 10 | 0.16 | 0.29 | 0.045 |
| 15 | 0.12 | 0.36 | 0.043 |
| 30 | 0.09 | 0.61 | 0.057 |

Release ratio of total buprenorphine:naltrexone from patch (13% NTX-EC/HPC film, 5% BUP PD) in water

| Time (min) | Amount of BUP released (μg) | Percentage of BUP released (%) | Amount of NTX released (μg) | Percentage of NTX released (%) | Ratio in water (total BUP:NTX) |
|---|---|---|---|---|---|
| 5 | 16.9 | 0.7 | 129.3 | 25.9 | 0.13 |
| 10 | 22.4 | 1.4 | 142.5 | 28.5 | 0.16 |
| 15 | 21.5 | 2.1 | 179.0 | 35.8 | 0.12 |
| 30 | 28.4 | 4.3 | 305.3 | 61.1 | 0.09 |

TABLE 4

Release ratio of total buprenorphine:naltrexone from patch (13% NTX-EC/HPC film, 5% BUP PD) in 0.1M phosphate buffer (pH 6.5)

| Time (min) | Ratio in phosphate buffer (total BUP:NTX) | NTX in phosphate buffer (mg/cm²) | BUP in phosphate buffer (mg/cm²) |
|---|---|---|---|
| 1 | 1.22 | 0.11 | 0.13 |
| 3 | 0.80 | 0.23 | 0.19 |
| 5 | 0.63 | 0.33 | 0.21 |

| Time (min) | Amount of BUP released (μg) | Percentage of BUP released (%) | Amount of NTX released (μg) | Percentage of NTX released (%) | Ratio in phosphate buffer (total BUP:NTX) |
|---|---|---|---|---|---|
| 1 | 134.4 | 19.2 | 109.7 | 21.9 | 1.22 |
| 3 | 185.8 | 26.5 | 233.2 | 46.6 | 0.80 |
| 5 | 212.2 | 30.3 | 337.6 | 67.5 | 0.63 |

Placebo adhesive layer, 15% Naltrexone-EC/HPC film, 5% Buprenorphine prodrug

TABLE 5

Release ratio of total buprenorphine:naltrexone from patch (placebo adhesive layer, 15% NTX-EC/HPC film, 5% BUP PD-15 mil thickness) in ethanol

| Time (min) | Amount of BUP released (μg) | Percentage of BUP released (%) | Amount of NTX released (μg) | Percentage of NTX released (%) | Ratio in ethanol (total BUP:NTX) |
|---|---|---|---|---|---|
| 10 | 844.0 | 100 | 332.4 | 22.2 | 2.54 |
| 15 | 868.5 | 100 | 589.5 | 39.3 | 1.47 |
| 30 | 819.9 | 100 | 1528.6 | 101.9 | 0.54 |

TABLE 6

Release ratio of total buprenorphine:naltrexone from patch (placebo adhesive layer, 15% NTX-EC/HPC film, 5% BUP PD-15 mil thickness) in water

| Time (min) | Amount of BUP released (μg) | Percentage of BUP released (%) | Amount of NTX released (μg) | Percentage of NTX released (%) | Ratio in water (total BUP:NTX) |
|---|---|---|---|---|---|
| 10 | 17.0 | 2.4 | 23.0 | 1.5 | 0.74 |
| 20 | 19.7 | 2.8 | 24.5 | 1.6 | 0.81 |
| 30 | 28.0 | 4.0 | 25.7 | 1.7 | 1.10 |

TABLE 7

Release ratio of total buprenorphine:naltrexone from patch (placebo adhesive layer, 15% NTX-EC/HPC film, 5% BUP PD-15 mil thickness) in 0.1M phosphate buffer (pH 6.5)

| Time (min) | Amount of BUP released (μg) | Percentage of BUP released (%) | Amount of NTX released (μg) | Percentage of NTX released (%) | Ratio in phosphate buffer (total BUP:NTX) |
|---|---|---|---|---|---|
| 1 | 66.4 | 9.5 | 21.6 | 1.4 | 3.08 |
| 3 | 100.2 | 14.3 | 46.2 | 3.1 | 2.17 |
| 5 | 128.5 | 18.4 | 143.7 | 9.6 | 0.89 |

TABLE 8

Release ratio of total buprenorphine:naltrexone from patch (placebo adhesive layer, 15% NTX-EC/HPC film, 5% BUP PD-20 mil thickness) in ethanol

| Time (min) | NTX conc (μg/mL) | ALL00160 (μg/mL) | Bup (μg/mL) | Total Bup (μg/mL) | Ratio in ethanol (total BUP:NTX) |
|---|---|---|---|---|---|
| 5 | 2.25 | 6.86 | 0.42 | 7.28 | 3.23 |
| 10 | 3.69 | 10.02 | 0.40 | 10.42 | 2.82 |
| 15 | 5.47 | 13.70 | 0.42 | 14.12 | 2.58 |
| 30 | 26.26 | 24.18 | 0.43 | 24.62 | 0.94 |

| Time (min) | Amount of BUP released (μg) | Percentage of BUP released (%) | Amount of NTX released (μg) | Percentage of NTX released (%) | Ratio in ethanol (total BUP:NTX) |
|---|---|---|---|---|---|
| 5 | 364.2 | 24.3 | 112.6 | 7.5 | 3.23 |
| 10 | 521.2 | 34.7 | 184.6 | 12.3 | 2.82 |
| 15 | 705.8 | 47.1 | 273.4 | 18.2 | 2.58 |
| 30 | 1230.8 | 82.1 | 1312.9 | 87.5 | 0.94 |

TABLE 9

Release ratio of total buprenorphine:naltrexone from patch (placebo adhesive layer, 15% NTX-EC/HPC film, 5% BUP PD-20 mil thickness) in water

| Time (min) | NTX conc (μg/mL) | Total Bup conc (μg/mL) | Ratio in water (total BUP:NTX) |
|---|---|---|---|
| 10 | 0.43 | 0.25 | 0.58 |
| 20 | 0.47 | 0.30 | 0.63 |
| 30 | 0.45 | 0.30 | 0.66 |
| 60 | 0.52 | 0.32 | 0.61 |
| 90 | 0.58 | 0.33 | 0.56 |
| 120 | 0.56 | 0.28 | 0.51 |

| Time (min) | Amount of BUP released (μg) | Percentage of BUP released (%) | Amount of NTX released (μg) | Percentage of NTX released (%) | Ratio in water (total BUP:NTX) |
|---|---|---|---|---|---|
| 10 | 12.3 | 0.8 | 21.3 | 1.4 | 0.58 |
| 20 | 14.9 | 1.0 | 23.6 | 1.6 | 0.63 |
| 30 | 15.0 | 1.0 | 22.6 | 1.5 | 0.66 |
| 60 | 16.0 | 1.1 | 26.1 | 1.7 | 0.61 |
| 90 | 16.4 | 1.1 | 29.1 | 1.9 | 0.56 |
| 120 | 14.2 | 0.9 | 28.0 | 1.9 | 0.51 |

TABLE 10

Release ratio of total buprenorphine:naltrexone from patch (placebo adhesive layer, 15% NTX-EC/HPC film, 5% BUP PD-20 mil thickness) in 0.1M phosphate buffer (pH 6.5)

| Time (min) | NTX conc (μg/mL) | Total Bup conc (μg/mL) | Ratio in phosphate buffer (total BUP:NTX) |
|---|---|---|---|
| 1 | 1.36 | 1.16 | 0.85 |
| 3 | 6.43 | 4.01 | 0.62 |
| 5 | 11.95 | 5.81 | 0.49 |

| Time (min) | Amount of BUP released (μg) | Percentage of BUP released (%) | Amount of NTX released (μg) | Percentage of NTX released (%) | Ratio in phosphate buffer (total BUP:NTX) |
|---|---|---|---|---|---|
| 1 | 23.2 | 1.5 | 27.2 | 1.8 | 0.85 |
| 3 | 80.1 | 5.3 | 128.6 | 8.6 | 0.62 |
| 5 | 116.2 | 7.7 | 238.9 | 15.9 | 0.49 |

10% Naltrexone-EC/HPC film, 7% Buprenorphine prodrug

TABLE 11

Release ratio of total buprenorphine:naltrexone from patch (10% NTX-EC/HPC film, 7% BUP PD) in ethanol

| Time (min) | Amount of BUP released (μg) | Percentage of BUP released (%) | Amount of NTX released (μg) | Percentage of NTX released (%) | Ratio in ethanol (total BUP:NTX) |
|---|---|---|---|---|---|
| 10 | 280.1 | 18.7 | 45.2 | 4.5 | 6.20 |
| 20 | 386.1 | 25.7 | 75.3 | 7.5 | 5.12 |
| 30 | 394.6 | 26.3 | 92.8 | 9.3 | 4.25 |
| 60 | 983.5 | 65.6 | 310.3 | 31.0 | 3.17 |
| 90 | 1025.7 | 68.4 | 442.9 | 44.3 | 2.32 |
| 120 | 1070.9 | 71.4 | 684.1 | 68.4 | 1.62 |

TABLE 12

Release ratio of total buprenorphine:naltrexone from patch
(10% NTX-EC/HPC film, 7% BUP PD) in water

| Time (min) | Amount of BUP released (μg) | Percentage of BUP released (%) | Amount of NTX released (μg) | Percentage of NTX released (%) | Ratio in water (total BUP:NTX) |
|---|---|---|---|---|---|
| 20 | 15.5 | 1.0 | 28.3 | 2.8 | 0.56 |
| 30 | 24.6 | 1.6 | 35.8 | 3.6 | 0.70 |
| 60 | 36.8 | 2.5 | 33.7 | 3.4 | 1.15 |
| 90 | 56.9 | 3.8 | 44.5 | 4.5 | 1.30 |
| 120 | 66.7 | 4.4 | 43.0 | 4.3 | 1.60 |

TABLE 13

Release ratio of total buprenorphine:naltrexone from patch
(10% NTX-EC/HPC film, 7% BUP PD) in 0.1M
phosphate buffer (pH 6.5)

| Time (min) | Amount of BUP released (μg) | Percentage of BUP released (%) | Amount of NTX released (μg) | Percentage of NTX released (%) | Ratio in phosphate buffer (total BUP:NTX) |
|---|---|---|---|---|---|
| 1 | 127.9 | 8.5 | 75.5 | 7.6 | 1.92 |
| 3 | 277.1 | 18.5 | 279.0 | 27.9 | 0.98 |
| 5 | 408.6 | 27.2 | 567.5 | 56.8 | 0.73 |

10% Naloxone-EC/HPC film, 7% Buprenorphine prodrug

TABLE 14

Release ratio of total buprenorphine:naloxone
from patch (10% NLX-EC/HPC film,
7% BUP PD) in ethanol (see also FIG. 7)

| Time (min) | Ratio in ethanol (total BUP:NLX) | NLX in ethanol (mg/cm²) | BUP in ethanol (mg/cm²) |
|---|---|---|---|
| 10 | 2.58 | 0.10 | 0.22 |
| 20 | 2.82 | 0.12 | 0.33 |
| 30 | 2.81 | 0.18 | 0.50 |
| 60 | 2.80 | 0.60 | 1.68 |
| 90 | 2.15 | 0.93 | 1.95 |
| 120 | 1.59 | 1.41 | 2.17 |

Release ratio of total buprenorphine:naloxone
from patch (10% NLX-EC/HPC film,
7% BUP PD) in ethanol

| Time (min) | Amount of BUP released (μg) | Percentage of BUP released (%) | Amount of NLX released (μg) | Percentage of NLX released (%) | Ratio in ethanol (total BUP:NLX) |
|---|---|---|---|---|---|
| 10 | 110.3 | 7.4 | 42.6 | 4.3 | 2.58 |
| 20 | 169.8 | 11.3 | 60.1 | 6.0 | 2.82 |
| 30 | 248.4 | 16.6 | 88.5 | 8.9 | 2.81 |
| 60 | 837.1 | 55.8 | 298.8 | 29.9 | 2.80 |
| 90 | 974.4 | 65.0 | 465.0 | 46.5 | 2.15 |
| 120 | 1082.0 | 72.1 | 702.5 | 70.3 | 1.59 |

TABLE 15

Release ratio of total buprenorphine:naloxone
from patch (10% NLX-EC/HPC film,
7% BUP PD) in water (see also FIG. 8)

| Time (min) | Ratio in water (total BUP:NLX) | NLX in water (mg/cm²) | BUP in water (mg/cm²) |
|---|---|---|---|
| 10 | 0 | 0.052 | 0.0 |
| 20 | 0.14 | 0.067 | 0.011 |
| 30 | 0.28 | 0.062 | 0.017 |
| 60 | 0.54 | 0.093 | 0.050 |
| 90 | 0.74 | 0.097 | 0.072 |
| 120 | 0.79 | 0.12 | 0.087 |

Release ratio of total buprenorphine:naloxone from patch
(10% NLX-EC/HPC film, 7% BUP PD) in water

| Time (min) | Amount of BUP released (μg) | Percentage BUP released (%) | Amount of NLX released (μg) | Percentage of NLX released (%) | Ratio in water (total BUP:NLX) |
|---|---|---|---|---|---|
| 10 | 0 | 0 | 25.8 | 2.6 | 0 |
| 20 | 5.3 | 0.4 | 33.4 | 3.3 | 0.14 |
| 30 | 8.4 | 0.6 | 30.7 | 3.1 | 0.28 |
| 60 | 24.6 | 1.6 | 46.9 | 4.7 | 0.54 |
| 90 | 35.9 | 2.4 | 48.1 | 4.8 | 0.74 |
| 120 | 43.6 | 2.9 | 54.9 | 5.5 | 0.79 |

TABLE 16

Release ratio of total buprenorphine:naloxone from
patch (10% NLX-EC/HPC film, 7% BUP PD)
in 0.1M phosphate buffer (pH 6.5)

| Time (min) | Ratio in phosphate buffer (total BUP:NLX) | NLX in phosphate buffer (mg/cm²) | BUP in phosphate buffer (mg/cm²) |
|---|---|---|---|
| 1 | 0.35 | 0.43 | 0.14 |
| 3 | 0.37 | 0.87 | 0.31 |
| 5 | 0.30 | 1.3 | 0.40 |

| Time (min) | Amount of BUP released (μg) | Percentage of BUP released (%) | Amount of NLX released (μg) | Percentage of NLX released (%) | Ratio in phosphate buffer (total BUP:NLX) |
|---|---|---|---|---|---|
| 1 | 137.7 | 9.2 | 424.7 | 42.5 | 0.35 |
| 3 | 310.3 | 20.7 | 865.6 | 86.6 | 0.37 |
| 5 | 393.5 | 26.2 | 1303.7 | 130.4 | 0.30 |

13% Naltrexone-EC/HPC film, 5% Buprenorphine

TABLE 17

Release ratio of buprenorphine:naltrexone from patch
(13% NTX-EC/HPC film, 5% BUP-F1) in ethanol

| Time (min) | Amount of BUP released (μg) | Percentage of BUP released (%) | Amount of NTX released (μg) | Percentage of NTX released (%) | Ratio in ethanol (total BUP:NTX) |
|---|---|---|---|---|---|
| 5 | 503.7 | 72.0 | 187.3 | 14.4 | 2.69 |
| 10 | 523.9 | 74.8 | 660.1 | 50.8 | 0.79 |
| 15 | 520.4 | 74.3 | 684.9 | 52.7 | 0.76 |
| 30 | 552.3 | 78.9 | 760.7 | 58.5 | 0.73 |

TABLE 18

Release ratio of buprenorphine:naltrexone from patch
(13% NTX-EC/HPC film, 5% BUP-F1) in water

| Time (min) | Amount of BUP released (µg) | Percentage of BUP released (%) | Amount of NTX released (µg) | Percentage of NTX released (%) | Ratio in water (total BUP:NTX) |
|---|---|---|---|---|---|
| 5 | 74.5 | 10.6 | 44.1 | 3.4 | 1.69 |
| 10 | 85.9 | 12.3 | 50.7 | 3.9 | 1.69 |
| 20 | 97.7 | 14.0 | 62.4 | 4.8 | 1.57 |
| 30 | 120.5 | 17.2 | 80.6 | 6.2 | 1.49 |
| 60 | 99.7 | 14.2 | 92.4 | 7.1 | 1.08 |
| 90 | 140.4 | 20.1 | 140.8 | 10.8 | 1.00 |
| 120 | 770.2 | 110.0 | 835.4 | 64.3 | 0.92 |

TABLE 19

Release ratio of buprenorphine:naltrexone from patch
(13% NTX-EC/HPC film, 5% BUP-F1)
in 0.1M phosphate buffer (pH 6.5)

| Time (min) | Amount of BUP released (µg) | Percentage of BUP released (%) | Amount of NTX released (µg) | Percentage of NTX released (%) | Ratio in phosphate buffer (total BUP:NTX) |
|---|---|---|---|---|---|
| 1 | 125.2 | 17.9 | 37.2 | 2.9 | 3.36 |
| 3 | 130.2 | 18.6 | 91.5 | 7.0 | 1.42 |
| 5 | 193.8 | 27.7 | 205.8 | 15.8 | 0.94 |

TABLE 20

Release ratio of buprenorphine:naltrexone from patch
(13% NTX-EC/HPC film, 5% BUP-F2) in ethanol

| Time (min) | Amount of BUP released (µg) | Percentage of BUP released (%) | Amount of NTX released (µg) | Percentage of NTX released (%) | Ratio in ethanol (total BUP:NTX) |
|---|---|---|---|---|---|
| 5 | 218.7 | 31.2 | 56.1 | 4.3 | 3.90 |
| 10 | 301.8 | 43.1 | 128.0 | 9.8 | 2.36 |
| 15 | 379.9 | 54.3 | 191.0 | 14.7 | 1.99 |
| 30 | 400.2 | 57.2 | 397.9 | 30.6 | 1.01 |

Example 2

Release kinetics in ethanol of a bi-layer patch system containing 5% naltrexone and a placebo adhesive layer separated by either an ethylene vinyl acetate (EVA) (3M™ Cotran™ 9728) or a prepared hydroxypropylcellulose (HPC) polymeric film. Table 21 and FIG. 9 depict the release of naltrexone from the EVA and HPC bi-layer patch.

TABLE 21

Release of naltrexone from a bi-layer patch in ethanol

| Time (min) | NTX Release in Ethanol EVA Film (mg/cm²) | NTX Release in Ethanol HPC Film (mg/cm²) |
|---|---|---|
| 10 | 0.014 | 0.02 |
| 30 | 0.022 | 0.062 |
| 60 | 0.032 | 0.127 |
| 90 | 0.043 | 0.17 |
| 120 | 0.051 | 0.17 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values is stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

We claim:

1. An abuse-resistant patch for transdermally delivering an opioid to a subject, comprising:
   (a) a backing layer;
   (b) a first layer underlying the backing layer, the first layer comprising: an opioid antagonist or opioid antagonist prodrug which is not transdermally delivered at therapeutic levels when the patch is used for transdermally administering the opioid to the subject; wherein the backing layer is substantially impermeable to the opioid antagonist or opioid antagonist prodrug of the first layer;
   (c) a second layer underlying the first layer, the second layer comprising:
      (i) an opioid selected from the group consisting of: an opioid agonist, an opioid agonist prodrug, an opioid agonist-antagonist and an opioid agonist-antagonist prodrug;
      (ii) a pressure sensitive adhesive; wherein the second layer is adapted to be in diffusional communication with the skin of the subject to transdermally administer a therapeutically effective amount of the opioid to the subject; and
   (d) a barrier layer located between the first and second layer, the barrier layer comprising: a water-insoluble polymeric material and a water-soluble polymer;
   wherein the release ratio is between about 1:60 and about 60:1 after the patch has been placed in ethanol, water or a phosphate buffer having a pH of about 6.5 for greater than about 30 seconds.

2. The abuse-resistant transdermal patch of claim 1, wherein the opioid agonist or opioid agonist prodrug is selected from the group consisting of: alfentanil, allylprodine, alphaprodine, anileridine, benzylmorphine, bezitramide, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, hydrocodone, hydromorphone, hydroxypethidine, isomethadone, ketobemidone, levorphanol, levomethadyl, levophenacylmorphan, lofentanil, meperidine, metazocine, methadone, metopon, morphine, myrophine, narceine, nicomorphine, norlevorphanol, normethadone, normorphine, norpipanone, opium, oxycodone, oxymorphone, papaveretum, phenadoxone, phenomorphan, phenazocine, phenoperidine, piminodine, piritramide, propheptazine, promedol, properidine, propoxyphene, sufentanil, tilidine and tramadol and prodrugs of any of the foregoing.

3. The abuse-resistant transdermal patch of claim 1, wherein the opioid agonist-antagonist or opioid agonist-antagonist prodrug is selected from the group consisting of: buprenorphine, butorphanol, dezocine, meptazinol, nalbuphine, nalorphine and pentazocine and prodrugs of any of the foregoing.

4. The abuse-resistant transdermal patch of claim 3, wherein the opioid agonist-antagonist is buprenorphine.

5. The abuse-resistant transdermal patch of claim 3, wherein the opioid agonist-antagonist prodrug is a buprenorphine prodrug.

6. The abuse-resistant transdermal patch of claim 5, wherein the buprenorphine prodrug is selected from the group consisting of:

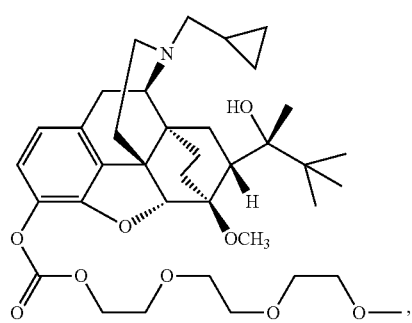

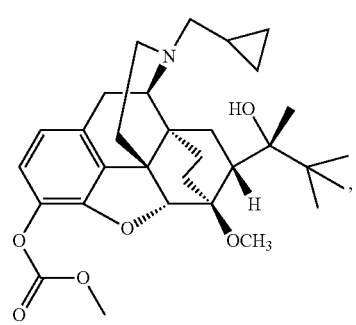

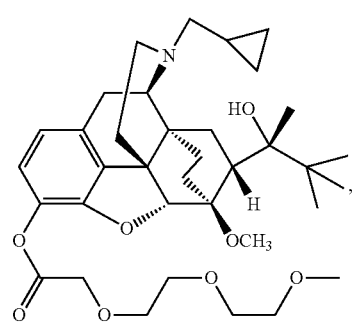

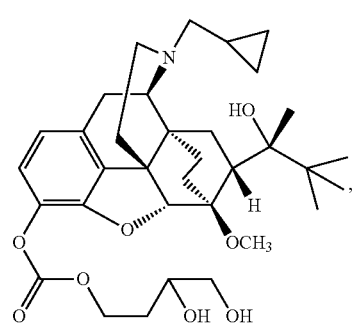

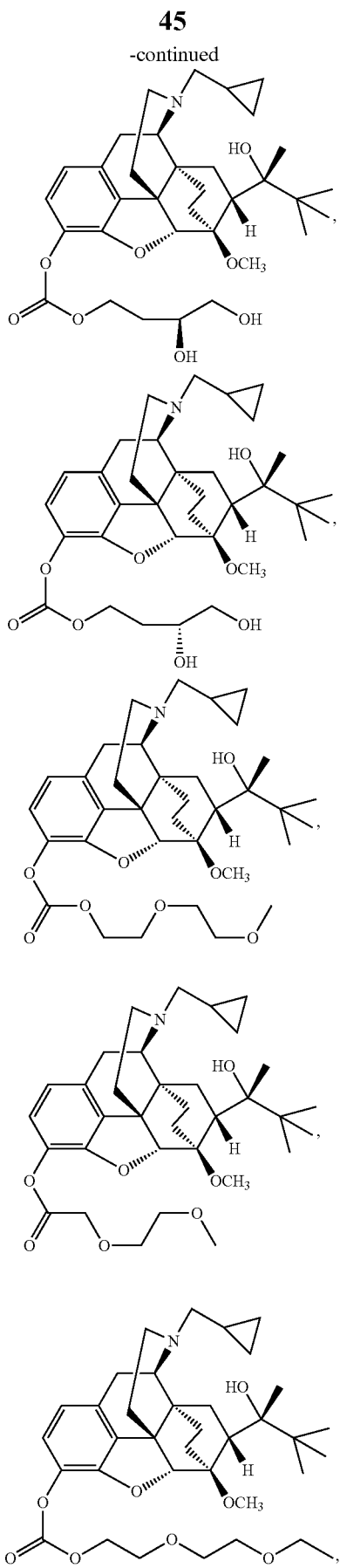
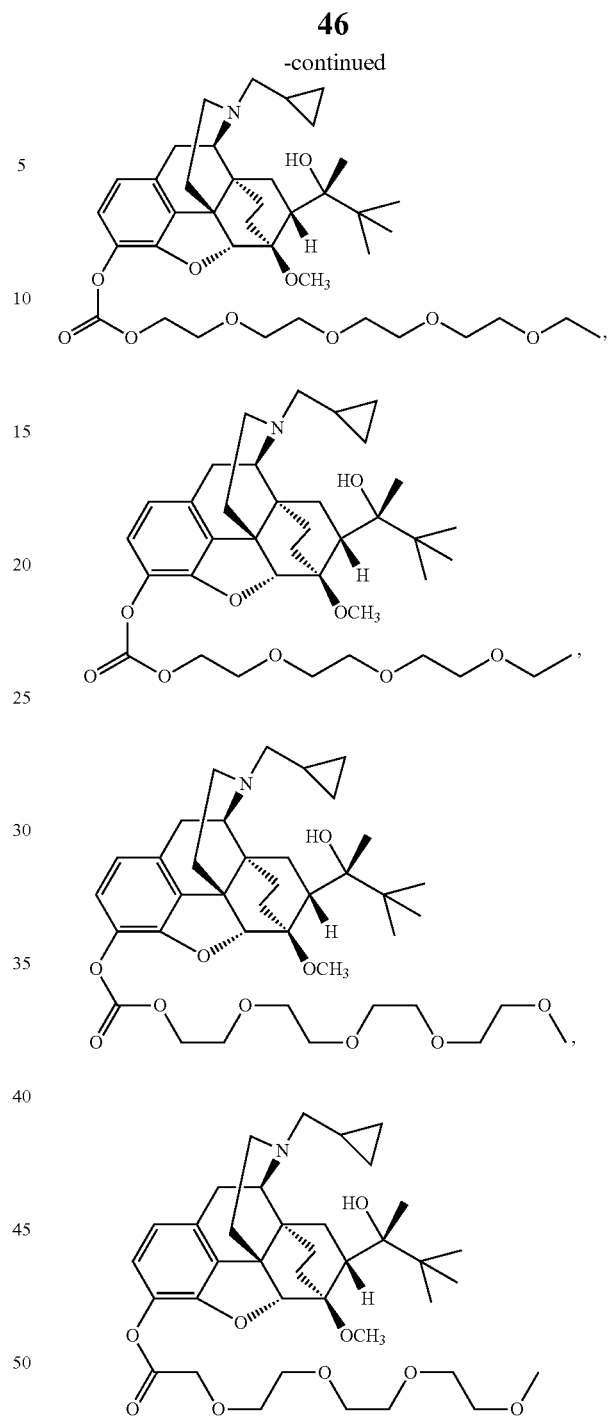

and salts of the foregoing.

7. The abuse-resistant transdermal patch of claim 1, wherein the opioid antagonist or the opioid antagonist prodrug is selected from the group consisting of: naltrexone, 6-beta-naltrexol, nalbuphine, nalmefene, naloxone, cyclazocine, levallorphan, cyclorphan and oxilorphan and prodrugs of any of the foregoing.

8. The abuse-resistant transdermal patch of claim 7, wherein the opioid antagonist is naltrexone or naloxone.

9. The abuse-resistant transdermal patch of claim 7, wherein the opioid antagonist prodrug is a naltrexone prodrug or a naloxone prodrug.

10. The abuse-resistant transdermal patch of claim 9, wherein the naltrexone prodrug is:

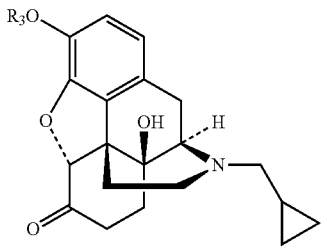

where R₃ is selected from the group consisting of:
—COC(CH₃)₃; —COCH(CH₃)₂; —COCH₂CH(CH₃)₂; —COCH(CH₂CH₃)₂; —CON(CH₂CH₃)₂; —CON(CH(CH₃)₂)₂; —COOCH(CH₃)₂;

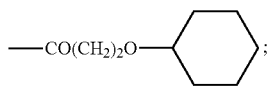

and
—CO(CH₂)₂OCH₃.

11. The abuse-resistant transdermal patch of claim 1, wherein the water-insoluble polymeric material is selected from the group consisting of: ethyl cellulose, cellulose derivatives, cellulose esters, ethylene-vinyl acetate copolymer, polyolefins, polyethylene, low density polyethylene, medium density polyethylene, high density polyethylene, polypropylene, ethylene-propylene copolymers, styrene polymers, polystyrene, vinyl polymers, polyvinyl acetate, acrylic polymers, ethylenemethyl acrylate copolymer, polymethyl acrylate, polyethyl acrylate, ethylene-acrylic acid copolymer, ethylene-ethylacrylate copolymer, homopolymers of acrylic acid, copolymers of acrylic acid, methyl methacrylate, methyl acrylic acid esters with quaternary ammonium groups and combinations of the foregoing.

12. The abuse-resistant transdermal patch of claim 1, wherein the water insoluble polymeric material is ethylcellulose.

13. The abuse-resistant transdermal patch of claim 1, wherein the water-soluble polymer is selected from the group consisting of: cellulose derivatives, hydroxypropylcellulose, hydroxypropylmethylcellulose, hydroxyethylcellulose, methyl cellulose, cellulose gum, sodium carboxymethylhydroxyethylcellulose, methylhydroxyethylcellulose, carboxyalkylcelluloses, carboxymethylcellulose, polyvinylpyrrolidone, polyethylene oxide, polysaccharides, dextran, polysialic acid, corn starch, agar, agarose, alginates, xanthan gums, heparin, chitin, chitosan, polyvinyl alcohol, polyethylene glycol, polyoxazoline, poly acryloylmorpholine and combinations of the foregoing.

14. The abuse-resistant transdermal patch of claim 1, wherein the water-soluble polymer is hydroxypropylcellulose.

15. The abuse-resistant transdermal patch of claim 1, wherein the first layer further comprises:
(a) optionally, a water-insoluble polymeric material selected from the group consisting of: ethyl cellulose, cellulose derivatives, cellulose esters, ethylene-vinyl acetate copolymer, polyolefins, polyethylene, low density polyethylene, medium density polyethylene, high density polyethylene, polypropylene, ethylene-propylene copolymers, styrene polymers, polystyrene, vinyl polymers, polyvinyl acetate, acrylic polymers, ethylenemethyl acrylate copolymer, polymethyl acrylate, polyethyl acrylate, ethylene-acrylic acid copolymer, ethylene-ethylacrylate copolymer, homopolymers of acrylic acid, copolymers of acrylic acid, methyl methacrylate, methyl acrylic acid esters with quaternary ammonium groups and combinations of the foregoing, and
(b) optionally, a water-soluble polymer selected from the group consisting of: cellulose derivatives, hydroxypropylcellulose, hydroxypropylmethylcellulose, hydroxyethylcellulose, methyl cellulose, cellulose gum, sodium carboxymethylhydroxyethylcellulose, methylhydroxyethylcellulose, carboxyalkylcelluloses, carboxymethylcellulose, polyvinylpyrrolidone, polyethylene oxide, polysaccharides, dextran, polysialic acid, corn starch, agar, agarose, alginates, xanthan gums, heparin, chitin, chitosan, polyvinyl alcohol, polyethylene glycol, polyoxazoline, poly acryloylmorpholine and combinations of the foregoing.

16. The abuse-resistant transdermal patch of claim 1, wherein the solvent is ethanol.

17. The abuse-resistant transdermal patch of claim 1, wherein the solvent is water.

18. The abuse-resistant transdermal patch of claim 1, wherein the solvent is a phosphate buffer having a pH of about 6.5.

19. The abuse-resistant transdermal patch of claim 1, wherein the opioid antagonist is naltrexone and the opioid is buprenorphine or a buprenorphine prodrug and wherein the release ratio is between about 1:1 and about 0.01:1.

20. The abuse-resistant transdermal patch of claim 1, wherein the opioid antagonist is a naltrexone prodrug and the opioid is buprenorphine or a buprenorphine prodrug and wherein the release ratio is between about 1:1 and about 0.01:1.

21. The abuse-resistant transdermal patch of claim 1, wherein the opioid antagonist is naloxone and the opioid is buprenorphine or a buprenorphine prodrug and wherein the release ratio is between about 4:1 and about 0.01:1.

22. The abuse-resistant transdermal patch of claim 1, wherein the opioid antagonist is a prodrug of naloxone and the opioid is buprenorphine or a buprenorphine prodrug and wherein the release ratio is between about 4:1 and about 0.01:1.

23. A method of treating a medical condition comprising affixing to the skin of the subject the transdermal patch of claim 1; wherein the medical condition is selected from the group consisting of: opioid dependence, alcohol dependence, polydrug addiction, pain, cocaine addiction, eating disorders and treatment-resistant depression.

24. The method of treating a medical condition of claim 23, wherein the opioid agonist or opioid agonist prodrug is selected from the group consisting of: alfentanil, allylprodine, alphaprodine, anileridine, benzylmorphine, bezitramide, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, hydrocodone, hydromorphone, hydroxypethidine, isomethadone, ketobemidone, levorphanol, levomethadyl, levophenacylmorphan, lofentanil, meperidine, metazocine, methadone, metopon, morphine, myrophine, narceine, nicomorphine, norlevorphanol, normethadone, normorphine, norpipanone, opium, oxycodone, oxymorphone, papaveretum, phenadoxone, phenomorphan, phenazocine, phenoperidine, piminodine, piritramide, propheptazine, promedol, properidine, propoxyphene, sufentanil, tilidine and tramadol and prodrugs of any of the foregoing.

25. The method of treating a medical condition of claim 23, wherein the opioid agonist-antagonist or opioid agonist-antagonist prodrug selected from the group consisting of: buprenorphine, butorphanol, dezocine, meptazinol, nalbuphine, nalorphine and pentazocine and prodrugs of any of the foregoing.

26. The method of treating a medical condition of claim 23, wherein the opioid antagonist or opioid antagonist prodrug is selected from the group consisting of: naltrexone, 6-beta-naltrexol, nalbuphine, nalmefene, naloxone, cyclazocine, levallorphan, cyclorphan and oxilorphan and prodrugs of any of the foregoing.

27. A method of making an abuse-resistant transdermal patch for delivering an opioid to a subject comprising the steps of:
   (a) applying a first layer to a substrate comprising a backing layer, the layer comprising: an opioid antagonist or opioid antagonist prodrug which is not transdermally delivered at therapeutic levels when the patch is used for transdermally administering the opioid;
   (b) applying a barrier layer to the first layer, the barrier layer comprising: a water-insoluble polymeric material and a water-soluble polymer; and
   (c) applying a second layer to the barrier layer, the second layer comprising:
      (i) an opioid selected from the group consisting of: an opioid agonist, a prodrug of an opioid agonist, an opioid agonist-antagonist and a prodrug of an opioid agonist-antagonist; and
      (ii) a pressure sensitive adhesive; wherein the second layer is adapted to be in diffusional communication with the skin of the subject to transdermally administer a therapeutically effective amount of the opioid to the subject;
   wherein the release ratio is between about 1:60 and about 60:1 after the patch has been placed in ethanol, water or a phosphate buffer having a pH of about 6.5 for greater than about 30 seconds.

28. The method of claim 27, wherein the opioid agonist or opioid agonist prodrug is selected from the group consisting of: alfentanil, allylprodine, alphaprodine, anileridine, benzylmorphine, bezitramide, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, hydrocodone, hydromorphone, hydroxypethidine, isomethadone, ketobemidone, levorphanol, levomethadyl, levophenacylmorphan, lofentanil, meperidine, metazocine, methadone, metopon, morphine, myrophine, narceine, nicomorphine, norlevorphanol, normethadone, normorphine, norpipanone, opium, oxycodone, oxymorphone, papaveretum, phenadoxone, phenomorphan, phenazocine, phenoperidine, piminodine, piritramide, propheptazine, promedol, properidine, propoxyphene, sufentanil, tilidine and tramadol and prodrugs of any of the foregoing.

29. The method of claim 27, wherein the opioid agonist-antagonist or opioid agonist-antagonist prodrug is selected from the group consisting of: buprenorphine, butorphanol, dezocine, meptazinol, nalbuphine, nalorphine and pentazocine and prodrugs of any of the foregoing.

30. The method of claim 27, wherein the opioid antagonist or opioid antagonist prodrug is selected from the group consisting of: naltrexone, 6-beta-naltrexol, nalbuphine, nalmefene, naloxone, cyclazocine, levallorphan, cyclorphan and oxilorphan and prodrugs of any of the foregoing.

* * * * *